US009687522B2

(12) United States Patent
Dhib-Jalbut

(10) Patent No.: US 9,687,522 B2
(45) Date of Patent: Jun. 27, 2017

(54) METHODS OF TREATING A SUBJECT AFFLICTED WITH AN AUTOIMMUNE DISEASE USING PREDICTIVE BIOMARKERS OF CLINICAL RESPONSE TO GLATIRAMER ACETATE THERAPY IN MULTIPLE SCLEROSIS

(71) Applicant: Suhayl Dhib-Jalbut, Princeton, NJ (US)

(72) Inventor: Suhayl Dhib-Jalbut, Princeton, NJ (US)

(73) Assignee: TEVA PHARMACEUTICAL INDUSTRIES, LTD., Petach-Tikva (IL)

( * ) Notice: Subject to any disclaimer, the term of this patent is extended or adjusted under 35 U.S.C. 154(b) by 397 days.

(21) Appl. No.: 14/266,506

(22) Filed: Apr. 30, 2014

(65) Prior Publication Data

US 2014/0322158 A1    Oct. 30, 2014

Related U.S. Application Data

(62) Division of application No. 13/049,720, filed on Mar. 16, 2011, now Pat. No. 8,759,302.

(60) Provisional application No. 61/340,427, filed on Mar. 16, 2010.

(51) Int. Cl.
*G01N 33/53* (2006.01)
*A61K 38/16* (2006.01)
*G01N 33/564* (2006.01)
*A61K 38/07* (2006.01)

(52) U.S. Cl.
CPC .............. *A61K 38/16* (2013.01); *A61K 38/07* (2013.01); *G01N 33/564* (2013.01); *G01N 2333/525* (2013.01); *G01N 2333/54* (2013.01); *G01N 2333/5428* (2013.01); *G01N 2333/96466* (2013.01); *G01N 2800/52* (2013.01); *G01N 2800/60* (2013.01)

(58) Field of Classification Search
CPC ................................ G01N 33/53; A61K 38/16
See application file for complete search history.

(56) References Cited

U.S. PATENT DOCUMENTS

| | | | |
|---|---|---|---|
| 5,800,808 A | 9/1998 | Konfino et al. | |
| 5,981,589 A | 11/1999 | Konfino et al. | |
| 6,048,898 A | 4/2000 | Konfino et al. | |
| 6,054,430 A | 4/2000 | Konfino et al. | |
| 6,214,791 B1 | 4/2001 | Arnon et al. | |
| 6,342,476 B1 | 1/2002 | Konfino et al. | |
| 6,362,161 B1 | 3/2002 | Konfino et al. | |
| 6,514,938 B1 | 2/2003 | Gad et al. | |
| 6,620,847 B2 | 9/2003 | Konfino et al. | |
| 6,800,285 B2 | 10/2004 | Rodriguez et al. | |
| 6,800,287 B2 | 10/2004 | Gad et al. | |
| 6,844,314 B2 | 1/2005 | Eisenbach-Schwartz et al. | |
| 6,939,539 B2 | 9/2005 | Konfino et al. | |
| 7,022,663 B2 | 4/2006 | Gilbert et al. | |
| 7,033,582 B2 | 4/2006 | Yong et al. | |
| 7,074,580 B2 | 7/2006 | Gad et al. | |
| 7,163,802 B2 | 1/2007 | Gad et al. | |
| 7,199,098 B2 | 4/2007 | Konfino et al. | |
| 7,279,172 B2 | 10/2007 | Aharoni | |
| 7,351,686 B2 | 4/2008 | Eisenbach-Schwartz et al. | |
| 7,407,936 B2 | 8/2008 | Eisenbach-Schwartz et al. | |
| 7,425,332 B2 | 9/2008 | Aharoni et al. | |
| 7,429,374 B2 | 9/2008 | Klinger | |
| 7,495,072 B2 | 2/2009 | Dolitzky et al. | |
| 7,560,100 B2 | 7/2009 | Pinchasi et al. | |
| 7,615,359 B2 | 11/2009 | Gad et al. | |
| 7,855,176 B1 | 12/2010 | Altman et al. | |
| 7,923,215 B2 | 4/2011 | Klinger | |

(Continued)

FOREIGN PATENT DOCUMENTS

WO    WO 98/30227    7/1998
WO    WO 00/05250    2/2000

(Continued)

OTHER PUBLICATIONS

Canadian Patent Application No. 2,606,194, filed Apr. 24, 2006 (Lancet et al.), Canadian counterpart of U.S. Appl. No. 11/409,590.
European Patent Application No. 06758673.5, filed Apr. 24, 2006 (European counterpart of U.S. Appl. No. 11/409,590).
PCT International Preliminary Report on Patentability issued Mar. 19, 2009 for International Application No. PCT/US2006/016036 (WO 2006/116602) (International counterpart of U.S. Appl. No. 11/409,509).
PCT International Search Report Issued Aug. 11, 2008 for International Application No. PCT/US2006/016036 (WO 2006/116602) (International counterpart of U.S. Appl. No. 11/409,509).
PCT Written Opinion issued Aug. 11, 2008 for International Application No. PCT/US2006/016036 (WO 2006/116602) (International counterpart of U.S. Appl. No. 11/409,509).
Feb. 18, 2010 Extended European Search Report in connection with European Patent Application No. 06758673.5.
Oct. 15, 2007 Office Action in connection with U.S. Appl. No. 11/409,590.

(Continued)

*Primary Examiner* — Prema Mertz
(74) *Attorney, Agent, or Firm* — John P. White; Gary J. Gershik; Cooper & Dunham LLP

(57) ABSTRACT

A method for treating a subject afflicted with an autoimmune disease with a pharmaceutical composition comprising glatiramer acetate and a pharmaceutically acceptable carrier, comprising the steps of administering a therapeutic amount of the pharmaceutical composition to the subject, determining whether the subject is a glatiramer acetate responder or a glatiramer acetate hypo-/non-responder by measuring the value of a biomarker selected from the group consisting of IL-10 concentration, IL-17 concentration, IL-18 concentration, TNF-α concentration, BDNF concentration, caspase-1 concentration, IL-10/IL-18 ratio and IL-10/IL-17 ratio in the blood of the subject, and comparing the measured value to a reference value for the biomarker to identify the subject as a glatiramer acetate responder or a glatiramer acetate hypo-/non-responder, and continuing the administration if the subject is identified as a glatiramer acetate responder, or modifying treatment of the subject if the subject is identified as a glatiramer acetate hypo-/non-responder.

19 Claims, 9 Drawing Sheets

(56) References Cited

U.S. PATENT DOCUMENTS

| | | |
|---|---|---|
| 2002/0037848 A1 | 3/2002 | Eisenbach-Schwartz |
| 2003/0170729 A1 | 9/2003 | Klinger |
| 2005/0170004 A1 | 8/2005 | Rosenberger |
| 2006/0052586 A1 | 3/2006 | Dolitzky |
| 2006/0172942 A1 | 8/2006 | Dolitzky |
| 2006/0240463 A1 | 10/2006 | Lancet |
| 2006/0264354 A1 | 11/2006 | Aharoni et al. |
| 2007/0021324 A1 | 1/2007 | Dolitzky |
| 2007/0021341 A1 | 1/2007 | Sela et al. |
| 2007/0037740 A1 | 2/2007 | Pinchasi et al. |
| 2007/0048794 A1 | 3/2007 | Gad et al. |
| 2007/0054857 A1 | 3/2007 | Pinchasi et al. |
| 2007/0059798 A1 | 3/2007 | Gad |
| 2007/0173442 A1 | 7/2007 | Vollmer |
| 2007/0248569 A1 | 10/2007 | Eisenbach-Schwartz |
| 2008/0085269 A1 | 4/2008 | Eisenbach-Schwartz |
| 2008/0207526 A1 | 8/2008 | Strominger |
| 2009/0053253 A1 | 2/2009 | Klinger |
| 2009/0149541 A1 | 6/2009 | Stark et al. |
| 2009/0214470 A1 | 8/2009 | Eisenbach-Schwartz et al. |
| 2010/0167983 A1 | 7/2010 | Kreitman et al. |
| 2010/0210817 A1 | 8/2010 | Gad et al. |
| 2010/0285600 A1 | 11/2010 | Lancet et al. |
| 2010/0298227 A1 | 11/2010 | Aharoni et al. |
| 2010/0305023 A1 | 12/2010 | Stark et al. |
| 2011/0046065 A1 | 2/2011 | Klinger |
| 2011/0060279 A1 | 3/2011 | Altman et al. |
| 2011/0066112 A1 | 3/2011 | Altman |
| 2011/0117115 A1 | 5/2011 | Eisenbach-Schwartz |
| 2011/0230413 A1 | 9/2011 | Dhib-Jalbut |

FOREIGN PATENT DOCUMENTS

| | | |
|---|---|---|
| WO | WO 00/18794 | 4/2000 |
| WO | WO 00/27417 | 5/2000 |
| WO | WO 01/60392 | 8/2001 |
| WO | WO 01/93828 | 12/2001 |
| WO | WO 01/97846 | 12/2001 |
| WO | WO 03/048735 | 6/2003 |
| WO | WO 2005/041933 | 6/2003 |
| WO | WO 2004/103297 | 2/2004 |
| WO | WO 2004/043995 | 5/2004 |
| WO | WO 2006/050122 | 5/2006 |
| WO | WO 2006/083608 | 8/2006 |
| WO | WO 2006/116602 | 11/2006 |
| WO | WO 2008/006026 | 1/2008 |
| WO | WO 2009/070298 | 6/2009 |

OTHER PUBLICATIONS

Jan. 15, 2008 Amendment in Response to Oct. 15, 2007 Office Action in connection with U.S. Appl. No. 11/409,590.
Mar. 14, 2008 Supplemental Response to Oct. 15, 2007 Office Action in connection with U.S. Appl. No. 11/409,590.
Jun. 18, 2008 Office Communication in connection with U.S. Appl. No. 11/409,590.
Jul. 18, 2008 Response to Jun. 18, 2008 Office Communication in connection with U.S. Appl. No. 11/409,590.
Oct. 24, 2008 Office Action in connection with U.S. Appl. No. 11/409,590.
Apr. 24, 2009 Amendment in Response to Oct. 24, 2008 Office Action in connection with U.S. Appl. No. 11/409,590.
Aug. 20, 2009 Final Office Action in connection with U.S. Appl. No. 11/409,590.
Opposition filed on Feb. 15, 2010 in connection with European Patent No. 1 459 065, granted Jul. 28, 2010 (European Application No. 02790028.1).
Opposition filed on Apr. 28, 2011 in connection with European Patent No. 1 115 743, granted May 26, 2009.
Opposition filed on Oct. 5, 2010 in connection with European Patent No. 1799703, granted Jan. 6, 2010.
Aharoni "Glatiramer acetate-specific T cells in the brain express T helper 2/3 cytokines and brain-derived neurotrophic factor in situ." PNAS Aug. 2003;100(24):14157-62.
Anderson, et al., (1992) "Revised estimate of the prevalence of multiple sclerosis in the United States." Ann Neurol., 31: 333-336.
Aranami et al. "Th17 Cells and autoimmune encephalomyelitis (EAE/MS)". Allergol Int. Jun. 2008; 57(2):115-20.
Beebe et al., "The role of IL-10 in autoimmune disease: systemic lupus erythematosus (SLE) and multiple sclerosis (MS)," Cytokine Growth factor rev. 12 (2002):403-412.
Begum-Haque et al., "Downregulation of IL-17 and IL-6 in the central nervous system by glatiramer acetate in experimental autoimmune encephalomyelitis." J Neuroimmunol. Nov. 15, 2008;204(1-2):58-65.
Bornstein, et al., "Treatments of Multiple Sclerosis with a Synthetic Polypeptide: Preliminary Results," Ann. Neurol., 1980, 8, 117 (Abstract).
Bornstein, et al., "Treatments of Multiple Sclerosis with a Synthetic Polypeptide: Preliminary Results," Trans. Am. Neurol. Assoc., 1980, 105, 348-350.
Bornstein, et al., "Multiple Sclerosis: Trial of a Synthetic Polypeptide," Ann. Neurol., 1982, 11, 317-319.
Bornstein, et al., "Clinical Trials of Copolymer 1 in Multiple Sclerosis,"Ann. N.Y. Acad. Sci. (USA), 1984, 366-372.
Bornstein, et al., "Clinical Trials of a Synthetic Polypeptide (Copolymer 1) for the treatment of Mutliple Sclerosis" in Gonsett et al., Immunological and Clinical Aspects of Multiple Sclerosis (MTP Press, The Hague, 1984) 144-150.
Bornstein, et al., "Multiple Sclerosis: Clinical Trials of a Synthetic Polypeptide, Copolymer 1," Neurol., 1985, 35, (Suppl. 1), 103 (Abstract).
Bornstein, "Cop 1 may be Beneficial for Patients with Exacerbating-remitting Form of Multiple Sclerosis," Adv. Ther. (USA), 1987, 4, 206 (Abstract) (Exhibit 45).
Bornstein, et al., "A Pilot Trial of Cop 1 in Exacerbating-remitting multiple Sclerosis," New Eng. J. Med., 1987, 317(7), 408-414.
Bornstein, et al., "Clinical Experience with COP-1 in Multiple Sclerosis," Neurol., 1988, 38(Suppl. 2) 66-69.
Bornstein et al., "Rationale for Immunomodulating Therapies of Multiple Sclerosis: Clinical Trial Design in Multiple Sclerosis Therapy," Neurol., 1988, vol. 38 (Suppl.2), pp. 80-81 [R].
Bornstein, et al., "Pilot Trial of COP-1 in Chronic Progressive Multiple Sclerosis: Preliminary Report," from the International Multiple Sclerosis Conference: An Update on Multiple Sclerosis, Roma (Italy), Sep. 15-17, 1988, in Elsevier Science Publisher, 1989, 225-232.
Bornstein, et. al., "Clinical Trials of Cop 1 in Multiple Sclerosis," in Handbook of Multiple Sclerosis (S.D. Cook Marcel Rekker, ed., 1990) 469-480.
Bornstein , et al., "A Placebo-controlled, Double-blind, Randomized Two-center, Pilot Trial of Cop 1 in Chronic Prgressive Multiple Sclerosis," Neurol., 1991, 41, 533-539.
Bornstein, et al., "Treatment of Multiple Sclerosis with Copolymer 1" in Treatment of Multiple Sclerosis: Trial Design, Results and Future Perspectives (Rudick R.A. & Goodkin D.E., eds., Springer Lerlag, London, 1992) 173-198.
Bornstein, "Clincal Experience: Hopeful Prospects in Multiple Sclerosis," Hospital Practice (Off. Ed.), 1992, vol. 27, No. 5, pp. L135-L158, 141-142, 145-158.
Brex et al., (2002) "A longitudinal study of abnormalities on MRI and disability from multiple sclerosis" Engl. J. Med., 3: 158-64.
Burger, Daniella et al., "Glatiramer acetate increases IL-1 receptor antagonist but decreases T cell-induced IL-B in human monocytes and multiple sclerosis," PNAS PNAS 2009 106 (11) 4355-4359 (2009); Early Edition 0812183106.
Cagguila et al., "Neurotrophic factors and clinical recovery in RR-MS," Scand J Immunol 2005, 62: 176-82.
Chen et al., "Glatiramer acetate induces a Th-2 biased response and cross-reactivity with myelin basic protein in patients with MS." Multiple Sclerosis 2001; 7:209-219.
Cohen et al., Identifying and treating patients with suboptimal responses. Neurology Dec. 28, 2004;63(12 Suppl 6):S33-40.
Comi G. et al., (2001) "European/Canadian Multicenter, Double-Blind, Randomized, Placebo-controlled study of the effects of

(56) References Cited

OTHER PUBLICATIONS

Glatiramer acetate on Magnetic resonance imaging-measured disease activity and burden in patients with relapsing multiple sclerosis" Ann. Neurol. 49:290-297.
Comi, et al. (2008) "Results from a phase III, one-year, randomized, double-blind, parallel-group, dose-comparison study with glatiramer acetate in relapsing-remitting multiple sclerosis". Mult Scler., 14(Suppl 1):S299.
Comi et al. Treatment with glatiramer acetate delays conversion to clinically definite multiple sclerosis (CDMS) in patients with clinically isolated syndromes (CIS). Neurology 2008; 71 (2): 153.
Cua et al., "Transgenic Interleukin-10 prevents induction of experimental autoimmune encephalomyelitis." J. Exp. Med. 189 120 (1999):1005-1010.
Dhib-Jalbut SS, Zhan M, Johnson KP, Martin R. Glatiramer acetate reactive blood mononuclear cells respond to myelin antigens with a Th-2 biased phenotype. J Neuroimmunology 2003; 140 :163-171.
Farina et al., "Treatment of multiple sclerosis with Copaxone (COP): Elispot assay detects COP-induced interleukin-4 and interferon-gamma response in blood cells." Brain. Apr. 2001;124(Pt 4):705-19.
Farina et al., "Immunological assay for assessing the efficacy of glatiramer acetate (Copaxone) in multiple sclerosis. A pilot study." J Neurol. Nov. 2002;249(11):1587-92.
Fridkis-Hareli, et al. "Direct binding of myelin basic protein and synthetic copolymer 1 to class II major histacompatibility complex molecules on living antigen-presenting cells-specificity promiscuity," Proc. Natl. Acad. Sci. USA. 91: 4872-6 (1994).
Fridkis-Hareli, et al., "Binding Motifs Copolymer 1 to Multiple Sclerosis- and Rheumatoid Arthritis-Associated HLA-DR Molecules" J. Immunol., 1999, 162: 4697-4704.
Fridkis-Hareli et al., "Binding of random copolymers of three amino acids to class II MCH molecules," Intl. Immunol., 1999, 11(5): 635-641.
Fridkis-Hareli et al., "Novel synthetic amino acid copolymers that inhibit autoantigen-specific T cell responses and suppress experimental autoimmune encephalomyelitis." J Clin Invest 109: 1635-1643 (2002).
Frohman et al., (2003) "The utility of MRI in suspected MS: report of Therapeutics and Technology Assessment Subcommittee of the American Academy of Neurology" Neurology Sep. 9, 61(5):602-11.
Gielen et al. "Increased brain-derived neurotrophic factor in white blood cells or RR MS patients" Scand J Immunol 2003, 57:493-97.
Gravel et al., "Adenoviral gene transfer of ciliary neurotrophic factor and brain-derived neurotrophic factor leads to long-term survival of axotomized motor neurons" Nat Med 1997; Jul 3(7): 765-770.
Grossman et al., "Pharmacogenetics of glatiramer acetate therapy for multiple sclerosis reveals drug-response markers" Pharmacogenetics and Genomics, 2007, 17: 657-666.
Groux et al., "Interleukin-10 induces a long-term antigen specific anergic state in human CD4+ T cells." J. exp. Med. 184 (1996):19-29.
Hirschorn et al., "A comprehensive review of genetic association studies" Genetics in Medicine, Mar. 2002, 4(2): 45-61.
Hong et al. Induction of CD4+CD254+ regulatory T cells by copolymer-I through activation of transcription factor Foxp3. Proc Nati Acad Sci May 3, 2005;102(18):6449-54. Epub Apr. 25, 2005.
Hussein et al. "Glatiramer acetate and IFN-beta act on dendritic cells in multiple sclerosis." J Neuro Immunol (2001)121:102-110.
Imitola et al., "Cytokines in multiple sclerosis: from bench to bedside" PharmacoIoannidis, et al. "Replication validity of genetic association studies" Nature Genetics, Nov. 2001, 29: 306-3091. Ther. 106 (2005):163-177.
Ioannidis, et al. "Replication validity of genetic association studies" Nature Genetics, Nov. 2001, 29: 306-309.
Jee et al., "CD4(+)CD25(+) regulatory T cells contribute to the therapeutic effects of glatiramer acetate in experimental autoimmune encephalomyelitis." Clin Immunol Oct. 2007;125(1):34-42. Epub Jul. 16, 2007.

Johnson D, Hafler DA, Fallis RJ, Lees MB, Brady RO, Quarles RH, Weiner HL., "Cell-mediated immunity to myelin-associated glycoprotein, proteolipid protein, and myelin basic protein in multiple sclerosis.", J Neuroimmunol. Nov. 1986;13 (1):99-108.
Kim et al. "Type 2 monocytes and microglia differentiation mediated by glatiramer acetate therapy in patients with multiple sclerosis," J Immunol (2004) 172:7144-7153.
Lucentini, "Second RNAi pathway emerges" The Scientist, Aug. 2004, 24: 20.
Martinelli et al. "Effects of glatiramer acetate on relapse rate and accumulated disability in multiple sclerosis: meta-analysis of three double-blind, randomized, placebo-controlled clinical trials." Muit Scler. Aug. 2003; 9(4):349-55.
Martinez et al., "IL-10 suppressor activity and ex-vivo Tr1 cell function are impaired in multiple sclerosis." Eur J Immunol. Feb. 2008;38(2):576-86.
McDonald et al., "Recommended diagnostic criteria for multiple sclerosis: guidelines from the International Panel on the diagnosis of multiple sclerosis." Ann Neurol. Jul. 2001;50(1):121-7.
Mikol et al., Lancet Neurol. Oct. 2008;7(10):903-14. Epub Sep. 11, 2008.
Noseworthy, et al. (2000) "Multiple sclerosis". N Engl J Med., 343: 938-52.
Physician's Desk Reference, Entry: "Copaxone," 2000, Medical Economics Co. Inc., Montvale, NJ, 3115.
Revel M., "Interferon-β in the treatment of relapsing-remitting multiple sclerosis" Pharmacol. Ther., 100(1):49-62 (2003).
Roncarlo "Type-1 regulatory cells." Immunol. Rev. 182(2001):68-80.
Rott et al., "Interleukin 10 prevents experimental allergic encephalomyelitis in rats." Eur. J. Immunol 24(1994):1434-1440.
Sarchielli et al. "Brain-derived neurotrophic factor in patients with multiple sclerosis". J Neuroimmunol Nov. 2002 132(1-2):180-88.
Sarchielli et al. "Production of brain-derived neurotrophic factor by mononuclear cells of patients with multiple sclerosis treated with glatiramer acetate, interferon-beta 1a, and high doses of immunoglobulins." Mult Scler Apr. 2007;13(3):313-31. Epub Jan. 29, 2007.
Stern et al., "Amino acid copolymer-specific IL-10 secretins regulatory T-cells that ameliorate autoimmune disease in mice." PNAS 2008, 105(13):5172-5176.
Tselis, et al., (2007) "Glatiramer acetate in the treatment of multiple sclerosis" Neuropsychiatric Dis Treat., 3(2): 259-67.
Valenzuela, et al., "Clinical response to glatiramer acetate correlates with modulation of IFN-gamma and IL-4 expression in multiple sclerosis." Mult Scler., Jul. 2007;13(6):754-62.
Valenzuela, et al. "Time course and functional capacity of glatiramer acetate-induced regulatory T-cells in multiple sclerosis patients." 23$^{rd}$ Congress of the European Committee for the Treatment and Research in Multiple Sclerosis (ECTRIMS), Oct. 12, 2007. (abstract).
Valenzuela "Predictive biomarkers of clinical response to Glatiramer Acetate (GA) therapy in Multiple Sclerosis" 2009, poster.
Vieira et al. "Glatiramer acetate (copolymer-1, copaxone) promotes Th2 cell development and increased IL-10 production through modulation of dendritic cells." J Immunol (2003) 170:4483-4488.
Weber et al. "Type II monocytes modulate T cell-mediated central nervous sytem autoimmune disease." Nat Med (2007) 13:935-943.
Wolinaky, et al. (2007) "Glatiramer acetate in primary progressive multiple sclerosis: Results of a multinational, multicenter, double-blind, placebo-controlled trial". Ann Neural. 61: 14-24.
Copaxone (glatiramer acetate injection), prescribing information, [Feb. 27, 2009] http://www.copaxone.com/pdf/prescribingInformation.pdf.
Clinical Trial Protocol No. 9001, Teva Pharmaceutical Industries, Ltd., first patient enrolled Oct. 23, 1991.
Clinical Trial Protocol No. 9002, Lemmon Co. and Teva Pharmaceutical Industries, Ltd., first patient enrolled Jun. 17, 1993.
U.S. Appl. No. 11/590,338, filed Oct. 30, 2006 (Pinchasi et al.).
Become Trial, Presented at the 23rd Congress of the European Committee for Treatment and Research in Multiple Sclerosis (ECTRIMS) in Prague, Czech Republic. (Oct. 11-14, 2007).

(56) References Cited

OTHER PUBLICATIONS

Bjartmar, et al. (2002) "Pathological mechanisms and disease progression of multiple sclerosis: therapeutic implications" *Drugs of Today*, 38(1): 17-29.

Comi G, Filippi M. Presented at: 60th Annual Meeting of the American Academy of Neurology: Apr. 12-19; Chicago, IL. Abstract LBS.003.

Felderhoff-Mueser, U. et al., (2005) "IL-18: A key playerin neuroinflamation and neurodegeneration" Trends in Neuroscience, 28(9): 487-93.

Guideline of Clinical investigation of medicinal products for the treatment of multiple sclerosis EMEA, London Nov. 16, 2006 CPMP/EWP/561/98 Rev.1.

Johnson, et al. (1998) "Extended Use of glatiramer acetate (Copaxone) is well tolerated and maintains its clinical effect on multiple sclerosis relapse rate and degree of disability." *Neurology*, 50: 701-708.

Neurostatus, Slightly modified from J.F. Kurtzke, Neurology 1983:33,1444-52, Ludwig Kappos, MD, Neurology, University Hospital 4031 Basel, Switzerland.

Wolinsky J.S. (2006) "The use of glatiramer acetate in the treatment of multiple sclerosis" Advances in Neurology 98: 273-292.

Valenzuela et al. "Predictive Biomarkers of Clinical Response to Glatiramer Acetate (GA) Therapy in Multiple Sclerosis (MS)", Neurology 72 Mar. 17, 2009 (Suppl 3).

Office Action issued Mar. 2, 2012 in connection with U.S. Appl. No. 13/049,720, filed Mar. 16, 2011.

Response to Office Action issued Mar. 2, 2012, filed Apr. 2, 2012, in connection with U.S. Appl. No. 13/049,720, filed Mar. 16, 2011.

Office Action issued May 16, 2012 in connection with U.S. Appl. No. 13/049,720, filed Mar. 16, 2011.

Response to Office Action issued May 16, 2012, filed Aug. 16, 2012, in connection with U.S. Appl. No. 13/049,720, filed Mar. 16, 2011.

Office Action issued Aug. 30, 2012 in connection with U.S. Appl. No. 13/049,720, filed Mar. 16, 2011.

Response to Office Action issued Aug. 30, 2012, filed Feb. 27, 2013, in connection with U.S. Appl. No. 13/049,720, filed Mar. 16, 2011.

Office Action issued Mar. 1, 2013 in connection with. U.S. Appl. No. 13/049,720, filed Mar. 16, 2011.

Response to Office Action issued Mar. 1, 2013, filed Mar. 19, 2013, in connection with U.S. Appl. No. 13/049,720, filed Mar. 16, 2011.

Office Action issued Mar. 26, 2013 in connection with U.S. Appl. No. 13/049,720, filed Mar. 16, 2011.

Office Action issued Jan. 10, 2014 in connection with U.S. Appl. No. 13/049,720, filed Mar. 16, 2011.

Response filed Jan. 24, 2014 in connection with U.S. Appl. No. 13/049,720, filed Mar. 16, 2011.

Response filed Jan. 27, 2014 in connection with U.S. Appl. No. 13/049,720, filed Mar. 16, 2011.

Notice of Allowance issued Jan. 31, 2014 in connection with U.S. Appl. No. 13/049,720, filed Mar. 16, 2011.

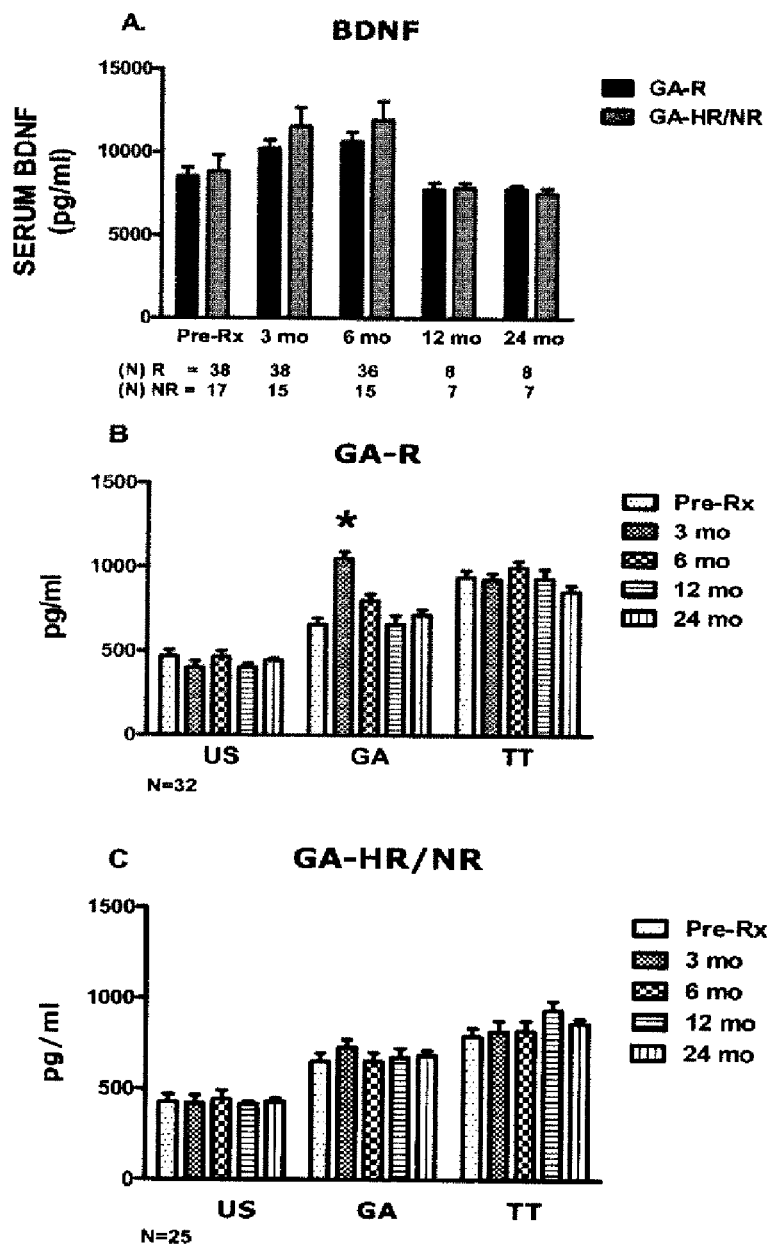
Figure 5A-C

METHODS OF TREATING A SUBJECT AFFLICTED WITH AN AUTOIMMUNE DISEASE USING PREDICTIVE BIOMARKERS OF CLINICAL RESPONSE TO GLATIRAMER ACETATE THERAPY IN MULTIPLE SCLEROSIS

This application is a divisional of U.S. Ser. No. 13/049,720, filed Mar. 16, 2011, now U.S. Pat. No. 8,759,302, issued Jun. 24, 2014, which claims the benefit of U.S. Provisional Application No. 61/340.427, filed Mar. 16, 2010, the entire contents of each of which are hereby incorporated by reference in their entirety into this application.

Throughout this application various publications are referenced by Arabic numeral in parenthesis. The full citation of the corresponding reference appears at the end of the specification before the claims. The disclosures of these publications in their entireties are hereby incorporated by reference into this application in order to more fully describe the state of the art to which this invention pertains.

BACKGROUND OF THE INVENTION

Multiple sclerosis (MS) is a chronic, debilitating autoimmune disease of the central nervous system (CNS) with either relapsing-remitting (RR) or progressive course leading to neurologic deterioration and disability. At time of initial diagnosis, RRMS is the most common form of the disease (1) which is characterized by unpredictable acute episodes of neurological dysfunction (relapses), followed by variable recovery and periods of clinical stability. The vast majority of RRMS patients eventually develop secondary progressive (SP) disease with or without superimposed relapses. Around 15% of patients develop a sustained deterioration of their neurological function from the beginning; this form is called primary progressive (PP) MS. Patients who have experienced a single clinical event (Clinically Isolated Syndrome or "CIS") and who show lesion dissemination on subsequent magnetic resonance imaging (MRI) scans according to McDonald's criteria, are also considered as having relapsing MS. (2)

With a prevalence that varies considerably around the world, MS is the most common cause of chronic neurological disability in young adults. (3,4) Anderson et al. estimated that there were about 350,000 physician-diagnosed patients with MS in the United States in 1990 (approx. 140 per 100,000 population). (5) It is estimated that about 2.5 million individuals are affected worldwide. (6) In general, there has been a trend toward an increasing prevalence and incidence of MS worldwide, but the reasons for this trend are not fully understood. (5)

Current therapeutic approaches consist of i) symptomatic treatment ii) treatment of acute relapses with corticosteroids and iii) treatment aimed to modify the course of the disease. Currently approved therapies target the inflammatory processes of the disease. Most of them are considered to act as immunomodulators but their mechanisms of action have not been completely elucidated. Immunosuppressants or cytotoxic agents are also used in some patients after failure of conventional therapies. Several medications have been approved and clinically ascertained as efficacious for the treatment of RR-MS; including BETASERON®, AVONEX® and REBIF®, which are derivatives of the cytokine interferon beta (IFNB), whose mechanism of action in MS is generally attributed to its immunomodulatory effects, antagonizing pro-inflammatory reactions and inducing suppressor cells. (7)

Glatiramer Acetate

Glatiramer acetate (GA) is the active substance in Copaxone®, a marketed product indicated for reduction of the frequency of relapses in patients with RRMS. Its effectiveness in reducing relapse rate and disability accumulation in RR-MS is comparable to that of other available immunomodulating treatments. (8, 9, 10) Glatiramer acetate consists of the acetate salts of synthetic polypeptides containing four naturally occurring amino acids: L-glutamic acid, L-alanine, L-tyrosine and L-lysine. The average molecular weight of glatiramer acetate is between 5,000 and 9,000 Daltons. At a daily standard dose of 20 mg, GA is generally well tolerated, however response to the drug is variable. In various clinical trials, GA reduced relapse rates and progression of disability in patients with RR-MS. The therapeutic effect of GA is supported by the results of magnetic resonance imaging (MRI) findings from various clinical centers (11), however there are no validated predictive biomarkers of response to GA treatment.

A possible initial mode of action of GA is associated with binding to MHC molecules and consequent competition with various myelin antigens for their presentation to T cells. (12) A further aspect of its mode of action is the potent induction of T helper 2 (Th2) type cells that presumably can migrate to the brain and lead to in situ bystander suppression. (13) It has been shown that GA treatment in MS results in the induction of GA-specific T cells with predominant Th2 phenotype both in response to GA and cross-reactive myelin antigens. (13, 14) Furthermore, the ability of GA-specific infiltrating cells to express anti-inflammatory cytokines such as IL-10 and transforming growth factor-beta (TGF-β) together with brain-derived neurotrophic factor (BDNF) seem to correlate with the therapeutic activity of GA in EAE. (15, 16, 17)

Clinical experience with GA consists of information obtained from completed and ongoing clinical trials and from post-marketing experience. The clinical program includes three double-blind, placebo-controlled studies in RRMS subjects treated with GA 20 mg/day. (18, 19, 20) A significant reduction in the number of relapses, compared with placebo, was seen. In the largest controlled study, the relapse rate was reduced by 32% from 1.98 under placebo to 1.34 under GA 20 mg. GA 20 mg has also demonstrated beneficial effects over placebo on MRI parameters relevant to RRMS. A significant effect in median cumulative number of Gd-enhancing lesions over 9 months of treatment (11 lesions in the 20 mg group compared to 17 lesions under placebo) was demonstrated.

The clinical program with GA also includes one double-blind study in chronic-progressive MS subjects, (21) one double-blind placebo-controlled study in primary progressive patients, (22) one double-blind placebo-controlled study in CIS patients (23) and numerous open-label and compassionate use studies, mostly in RRMS. The clinical use of GA has been extensively reviewed and published in the current literature. (24, 25, 26, 27)

To determine whether GA-induced immunological changes in vivo can predict the clinical response to GA therapy, we conducted a prospective 2-year study in which cytokine levels, BDNF production and lymphocyte proliferation in ex-vivo PBMC of GA-treated MS patients were correlated with the clinical response to the drug at the end of at least 2 years of therapy. The laboratory personnel were blinded as to whether the patients were clinical responders or hypo/non-responders.

SUMMARY OF THE INVENTION

The present invention provides a method for treating a subject afflicted with an autoimmune disease with a pharmaceutical composition comprising glatiramer acetate and a pharmaceutically acceptable carrier, comprising the steps of:
  a) administering a therapeutic amount of the pharmaceutical composition to the subject;
  b) determining whether the subject is a glatiramer acetate responder or a glatiramer acetate hypo-/non-responder by measuring the value of a biomarker selected from the group consisting of IL-10 concentration, IL-17 concentration, IL-18 concentration, TNF-α concentration, BDNF concentration, caspase-1 concentration, IL-10/IL-18 ratio and IL-10/IL-17 ratio in the blood of the subject, and comparing the measured value to a reference value for the biomarker to identify the subject as a glatiramer acetate responder or a glatiramer acetate hypo-/non-responder; and
  c) continuing the administration if the subject is identified as a glatiramer acetate responder, or modifying treatment of the subject if the subject is identified as a glatiramer acetate hypo-/non-responder.

The present invention also provides a method for monitoring treatment of an autoimmune disease in a subject afflicted therewith, comprising:
  a) administering to the subject a therapeutic amount of a pharmaceutical composition comprising glatiramer acetate and a pharmaceutically acceptable carrier;
  b) evaluating whether administration of the pharmaceutical composition causes a change in the value of a biomarker selected from the group consisting of IL-10 concentration, IL-17 concentration, IL-18 concentration, TNF-α concentration, BDNF concentration, caspase-1 concentration, IL-10/IL-18 ratio and IL-10/IL-17 ratio in the blood of the subject.

The present invention also provides a method for determining clinical responsiveness to glatiramer acetate therapy in a subject afflicted with an autoimmune disease and receiving glatiramer acetate, the method comprising measuring the value of a biomarker selected from the group consisting of IL-10 concentration, IL-17 concentration, IL-18 concentration, TNF-α concentration, BDNF concentration, caspase-1 concentration, IL-10/IL-18 ratio and IL-10/IL-17 ratio in the blood of the subject, and comparing the measured value to a reference value for the biomarker, to thereby evaluate clinical responsiveness to glatiramer acetate.

The present invention also provides a method to identify a composition useful for the treatment of an autoimmune disease in a subject, comprising:
  a) administering the composition to the subject;
  b) evaluating whether administration of the composition causes a change in the value of a biomarker selected from the group consisting of IL-10 concentration, IL-17 concentration, IL-18 concentration, TNF-α concentration, BDNF concentration, caspase-1 concentration, unstimulated IL-4/IFN-γ ratio, IL-10/IL-18 ratio and IL-10/IL-17 ratio in the blood of the subject; and
  c) identifying the composition as useful for the treatment of the autoimmune disease in the subject if the change in the value of the biomarker is associated with treatment of the autoimmune disease.

The present invention also provides a method to identify a dose of a composition useful for the treatment of an autoimmune disease comprising:
  a) administering the composition to subjects at different doses, wherein the composition causes a change in the value of a biomarker selected from the group consisting of IL-10 concentration, IL-17 concentration, IL-18 concentration, TNF-α concentration, BDNF concentration, caspase-1 concentration, unstimulated IL-4/IFN-γ ratio, IL-10/IL-18 ratio and IL-10/IL-17 ratio in the blood of the subject;
  b) evaluating the change in the value of the biomarker at the different doses of the composition; and
  c) identifying a dose of the composition that elicits the desired magnitude of change in the value of the biomarker.

The present invention also provides a method for treating a subject afflicted with an autoimmune disease with a pharmaceutical composition comprising glatiramer acetate and a pharmaceutically acceptable carrier, comprising the steps of:
  a) administering a therapeutic amount of the pharmaceutical composition to the subject;
  b) measuring the value of an unstimulated IL-4/IFN-γ ratio in the blood of the subject and comparing the measured value to a reference value for the unstimulated IL-4/IFN-γ ratio;
  c) identifying the subject as a glatiramer acetate responder if the measured value is greater than the reference value or as a glatiramer acetate hypo-/non-responder if the measured value is less than or equal to the reference value; and
  d) continuing the administration if the subject is identified as a glatiramer acetate responder, or modifying treatment of the subject if the subject is identified as a glatiramer acetate hypo-/non-responder.

Figure 1:
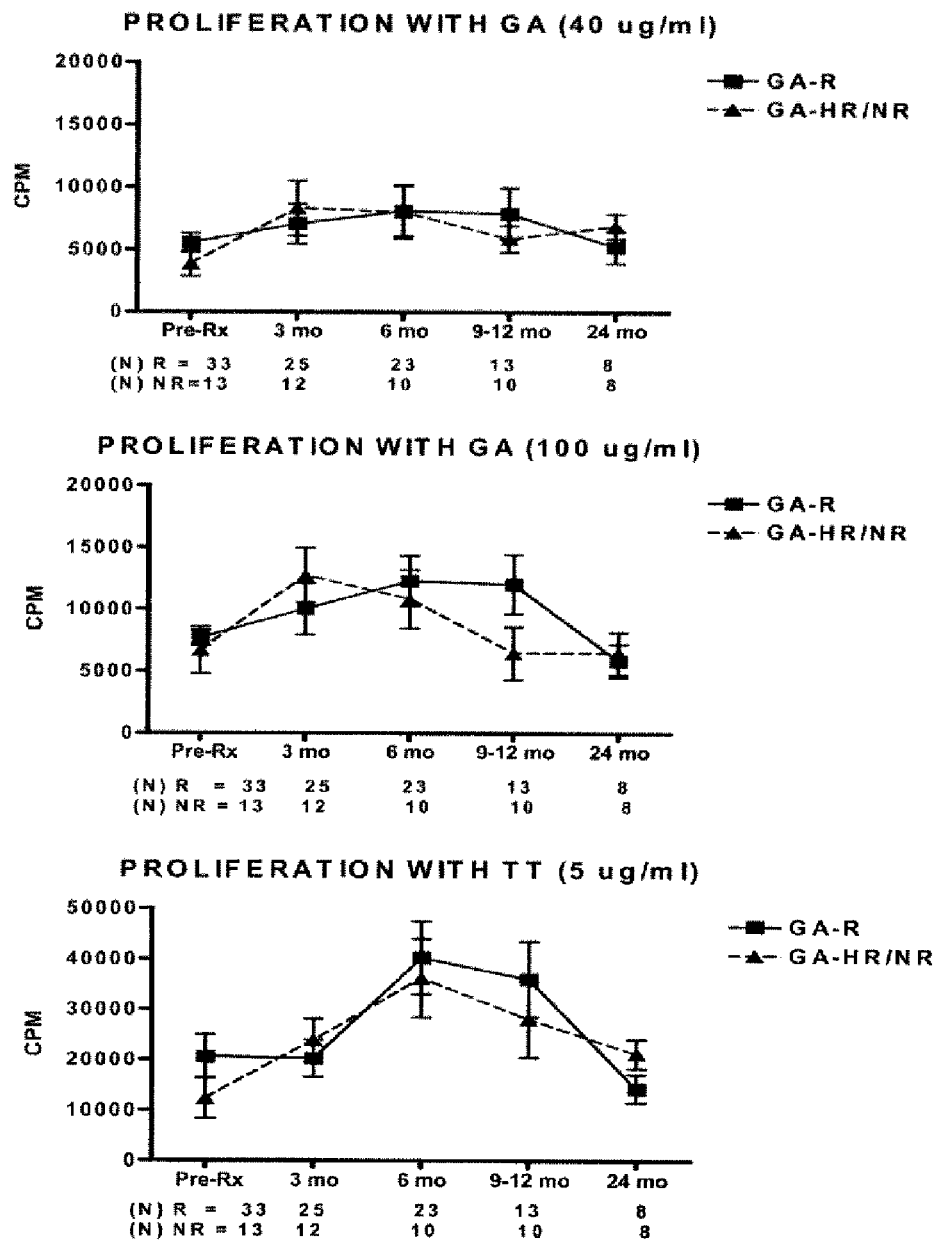
FIG. 1.

Lymphoproliferative responses to GA and TT in the GA-R and GA-HR/NR groups.

Peripheral blood mononuclear cells were seeded in 96 well U-bottom micro titer plate in the absence or presence of antigen (GA at 40 and 100 μg/ml) and TT (5 μg/ml) as control antigen at pre-treatment and at various time points during treatment. Supernatants were collected from these cultured cells at days 1, 3 and 5 for various analysis. Lymphoproliferation was performed at baseline (pre-treatment) and at 3, 6, 9-12 and 24 months during GA treatment. The graphs represent mean proliferation responses in CPM and standard deviation for each of the two groups at different time points. (N) indicates the number of subjects studied at each time point in the two groups. Background proliferation activity (Unstimulated condition) range was 190-700 CPM.

FIG. 2A-B.

Serum Cytokines and Caspase-1 Levels.

Serum IFN-γ, TNF-α, IL-18, IL-10, IL-4, TGF-β and caspase-1 Levels were measured by ELISA at baseline (pre-treatment), 3 months, 6 months, 12 months and 24 months during treatment with GA.

FIG. 3A-B.

Cytokine Levels in PBMC Supernatants.

IL-10, IL-17 and IL-18 levels as measured by ELISA in PBMC supernatants after 5-day culture with GA (40 μg/ml), TT (5 μg/ml) and unstimulated cells. Assays were performed at baseline (pre-treatment), 3 months and 6 months, 12 months and 24 months during treatment with GA.

FIG. 4.

IL-4/IFN-γ ratio in unstimulated and CD3/CD28 stimulated PBMC for the GA-R and GA-HR/NR groups at baseline (pre-treatment) and at 3, 6, 9-12 and 24 months during GA treatment.

FIG. 5A-C.

Brain-Derived Neurotrophic Factor (BDNF) in serum (A) and PBMC supernatant (B and C) as measured by ELISA at baseline (pre-treatment), 3 months, 6 months, 12 months and 24 months during treatment with GA.

FIG. 6A-B.

Receiver Operating Characteristic (ROC) curves for selected assays. (A) shows ROC curves for continuous measurements of change from baseline. Measurements are at 6 months except as specified. "Combination" refers to a best-fitting logistic regression using change in IL-4, IL-18, Caspase, and TNF-alpha from baseline to 6 months. (B) shows ROC curves for dichotomized measurements. Single assay curves are determined using optimism-corrected sensitivity and specificity. "Combination" here refers a test based only a count of whether IL-18 and Caspase levels are below their thresholds.

DETAILED DESCRIPTION OF THE INVENTION

The present invention provides a method for treating a subject afflicted with an autoimmune disease with a pharmaceutical composition comprising glatiramer acetate and a pharmaceutically acceptable carrier, comprising the steps of:
  a) administering a therapeutic amount of the pharmaceutical composition to the subject;
  b) determining whether the subject is a glatiramer acetate responder or a glatiramer acetate hypo-/non-responder by measuring the value of a biomarker selected from the group consisting of IL-10 concentration, IL-17 concentration, IL-18 concentration, TNF-α concentration, BDNF concentration, caspase-1 concentration, IL-10/IL-18 ratio and IL-10/IL-17 ratio in the blood of the subject, and comparing the measured value to a reference value for the biomarker to identify the subject as a glatiramer acetate responder or a glatiramer acetate hypo-/non-responder; and
  c) continuing the administration if the subject is identified as a glatiramer acetate responder, or modifying treatment of the subject if the subject is identified as a glatiramer acetate hypo-/non-responder.

The present invention also provides a method for monitoring treatment of an autoimmune disease in a subject afflicted therewith, comprising:
  a) administering to the subject a therapeutic amount of a pharmaceutical composition comprising glatiramer acetate and a pharmaceutically acceptable carrier;
  b) evaluating whether administration of the pharmaceutical composition causes a change in the value of a biomarker selected from the group consisting of IL-10 concentration, IL-17 concentration, IL-18 concentration, TNF-α concentration, BDNF concentration, caspase-1 concentration, IL-10/IL-18 ratio and IL-10/IL-17 ratio in the blood of the subject.

The present invention also provides a method for determining clinical responsiveness to glatiramer acetate therapy in a subject afflicted with an autoimmune disease and receiving glatiramer acetate, the method comprising measuring the value of a biomarker selected from the group consisting of IL-10 concentration, IL-17 concentration, IL-18 concentration, TNF-α concentration, BDNF concentration, caspase-1 concentration, IL-10/IL-18 ratio and IL-10/IL-17 ratio in the blood of the subject, and comparing the measured value to a reference value for the biomarker, to thereby evaluate clinical responsiveness to glatiramer acetate.

The present invention also provides a method to identify a composition useful for the treatment of an autoimmune disease in a subject, comprising:
  a) administering the composition to the subject;
  b) evaluating whether administration of the composition causes a change in the value of a biomarker selected from the group consisting of IL-10 concentration, IL-17 concentration, IL-18 concentration, TNF-α concentration, BDNF concentration, caspase-1 concentration, unstimulated IL-4/IFN-γ ratio, IL-10/IL-18 ratio and IL-10/IL-17 ratio in the blood of the subject; and
  c) identifying the composition as useful for the treatment of the autoimmune disease in the subject if the change in the value of the biomarker is associated with treatment of the autoimmune disease.

The present invention also provides a method to identify a dose of a composition useful for the treatment of an autoimmune disease comprising:
  a) administering the composition to subjects at different doses, wherein the composition causes a change in the value of a biomarker selected from the group consisting of IL-10 concentration, IL-17 concentration, IL-18 concentration, TNF-α concentration, BDNF concentration, caspase-1 concentration, unstimulated IL-4/IFN-γ ratio, IL-10/IL-18 ratio and IL-10/IL-17 ratio in the blood of the subject;
  b) evaluating the change in the value of the biomarker at the different doses of the composition; and
  c) identifying a dose of the composition that elicits the desired magnitude of change in the value of the biomarker.

In the methods disclosed herein, comparing the measured value to a reference value may include a step of identifying the subject as a glatiramer acetate responder if the measured value of the IL-10 concentration, BDNF concentration, IL-10/IL-18 ratio, or IL-10/IL-17 ratio is greater than the reference value.

In the methods disclosed herein, comparing the measured value to a reference value may include a step of identifying the subject as a glatiramer acetate responder if the measured value of the IL-17 concentration, IL-18 concentration or caspase-1 concentration is less than the reference value.

In the methods disclosed herein, comparing the measured value to a reference value may include a step of identifying the subject as a glatiramer acetate hypo-/non-responder if the measured value of the IL-10 concentration, IL-10/IL-17 ratio, or IL-10/IL-18 ratio is less than the reference value, or if the IL-17 concentration is greater than or equal to the reference value.

The present invention also provides a method for treating a subject afflicted with an autoimmune disease with a pharmaceutical composition comprising glatiramer acetate and a pharmaceutically acceptable carrier, comprising the steps of:
  a) administering a therapeutic amount of the pharmaceutical composition to the subject;

b) measuring the value of an unstimulated IL-4/IFN-γ ratio in the blood of the subject and comparing the measured value to a reference value for the unstimulated IL-4/IFN-γ ratio;

c) identifying the subject as a glatiramer acetate responder if the measured value is greater than the reference value or as a glatiramer acetate hypo-/non-responder if the measured value is less than or equal to the reference value; and d) continuing the administration if the subject is identified as a glatiramer acetate responder, or modifying treatment of the subject if the subject is identified as a glatiramer acetate hypo-/non-responder.

In an embodiment of the methods, the biomarker is unstimulated IL-4/IFN-γ ratio, and the change in the value of the biomarker is an increase in the value of the biomarker.

In an embodiment of the methods, the autoimmune disease is a B-cell mediated autoimmune disease, a T-cell mediated autoimmune disease, an arthritic condition, a demyelinating disease, an inflammatory disease, or an inflammatory bowel disease.

In an embodiment of the methods, the autoimmune disease is selected from the group consisting of rheumatoid arthritis, Crohn's disease, colitis, myasthenia gravis, and multiple sclerosis.

In an embodiment of the methods, said composition comprises an active agent selected from the group consisting of glatiramer acetate, a glatiramer acetate-related peptide and a glatiramer acetate-related polypeptide.

In an embodiment of the methods, said composition comprises a glatiramer acetate-related peptide or a glatiramer acetate-related polypeptide.

In an embodiment of the methods, said composition comprises glatiramer acetate.

In an embodiment of the methods, an increase in IL-10 concentration, BDNF concentration, IL-10/IL-18 ratio, or IL-10/IL-17 ratio is associated with a subject being a responder to glatiramer acetate treatment.

In an embodiment of the methods, the concentration or ratio is a serum concentration or serum ratio.

In an embodiment of the methods, the concentration or ratio is a PBMC supernatant concentration or PBMC supernatant ratio.

In an embodiment of the methods, the increase in IL-10 concentration, BDNF concentration, IL-10/IL-18 ratio, or IL-10/IL-17 ratio is observed at 3 months.

In an embodiment of the methods, the increase in IL-10 concentration, BDNF concentration, IL-10/IL-18 ratio, or IL-10/IL-17 ratio is observed at 6 months.

In an embodiment of the methods, at 6 months a serum IL-10 concentration greater than or equal to 56 pg/ml is associated with a subject being a responder to glatiramer acetate treatment.

In an embodiment of the methods, at 6 months a supernatant IL-10 concentration greater than or equal to 246 pg/ml is associated with a subject being a responder to glatiramer acetate treatment.

In an embodiment of the methods, at 3 months a supernatant BDNF concentration greater than or equal to 2.4 pg/ml is associated with a subject being a responder to glatiramer acetate treatment.

In an embodiment of the methods, at 6 months a supernatant IL-10/IL-17 ratio greater than or equal to 2.03 is associated with a subject being a responder to glatiramer acetate treatment.

In an embodiment of the methods, at 6 months a supernatant IL-10/IL-18 ratio greater than or equal to 0.74 is associated with a subject being a responder to glatiramer acetate treatment.

In an embodiment of the methods, at 3 months an unstimulated IL-4/IFN-γ ratio greater than or equal to 0.24 is associated with a subject being a responder to glatiramer acetate treatment.

In an embodiment of the methods, at 6 months a serum IL-10 concentration below 52 pg/ml is associated with a subject being a non-responder to glatiramer acetate treatment.

In an embodiment of the methods, at 6 months a supernatant IL-10/IL-17 ratio below 2.03 is associated with a subject being a non-responder to glatiramer acetate treatment.

In an embodiment of the methods, at 6 months a serum IL-10/IL-18 ratio below 0.74 is associated with a subject being a non-responder to glatiramer acetate treatment.

In an embodiment of the methods, a decrease in IL-17 concentration, IL-18 concentration or caspase-1 concentration is associated with a subject being a responder to glatiramer acetate treatment.

In an embodiment of the methods, the concentration or ratio is a serum concentration or serum ratio.

In an embodiment of the methods, the concentration or ratio is a PBMC supernatant concentration or PBMC supernatant ratio.

In an embodiment of the methods, the decrease in IL-17 concentration, IL-18 concentration or caspase-1 concentration is observed at 3 months.

In an embodiment of the methods, the decrease in IL-17 concentration, IL-18 concentration or caspase-1 concentration is observed at 6 months.

In an embodiment of the methods, at 6 months a supernatant IL-17 concentration less than or equal to 95 pg/ml is associated with a subject being a responder to glatiramer acetate treatment.

In an embodiment of the methods, at 6 months a serum IL-18 concentration less than or equal to 215 pg/ml is associated with a subject being a responder to glatiramer acetate treatment.

In an embodiment of the methods, at 6 months a serum caspase-1 concentration is less than or equal to 208 pg/ml is associated with a subject being a responder to glatiramer acetate treatment.

In an embodiment of the methods, at 6 months a supernatant IL-17 concentration greater than or equal to 135 pg/ml is associated with a subject being a non-responder to glatiramer acetate treatment.

In an embodiment of the methods, more than one biomarker is measured and/or evaluated.

In an embodiment of the methods, the biomarker is a combined biomarker consisting of IL-18 concentration and caspase-1 concentration.

In an embodiment of the methods, the biomarker is selected from the group consisting of IL-10 concentration, IL-17 concentration, IL-18 concentration, TNF-α concentration, BDNF concentration, caspase-1 concentration, IL-10/IL-18 ratio and IL-10/IL-17 ratio.

The present invention further provides methods for treating and preventing autoimmune diseases in a subject which include administering a therapeutically effective amount of a composition having an active agent which is selected from the group consisting of glatiramer acetate, a glatiramer acetate-related peptide and a glatiramer acetate-related polypeptide.

Autoimmune diseases contemplated by the present invention include either cell-mediated disease (e.g., T-cell) or antibody mediated (e.g., B-cell) disorders. Such disorders can be, Inter alia, arthritic conditions, demyelinating diseases and inflammatory diseases. For example, autoimmune diseases contemplated herein include multiple sclerosis, autoimmune hemolytic anemia, autoimmune oophoritis, autoimmune thyroiditis, autoimmune uveoretinitis, Crohn's disease, chronic immune thrombocytopenic purpura, colitis, contact sensitivity disease, diabetes mellitus, Grave's disease, Guillain-Barre's syndrome, Hashimoto's disease, idiopathic myxedema, myasthenia gravis, psoriasis, *pemphigus vulgaris*, rheumatoid arthritis, or systemic lupus erythematosus. The present compositions can be used to treat one or more of these diseases.

The "arthritic condition" contemplated herein is a condition wherein at least one symptom of rheumatoid arthritis is observed in at least one joint of a mammal, for example in a shoulder, knee, hip, backbone or a digit of the mammal. Examples of arthritic conditions include "polyarthritis", which is an arthritic condition that affects more than a single joint; "juvenile arthritis", an arthritic condition of humans under the age of 21; and Felty's syndrome, which can include the symptoms of neutropenia, splenomegaly, weight loss, anemia, lymphadenopathy, and pigment spots on the skin.

In one embodiment, any autoimmune disease can be treated by the present polypeptides so long as the contemplated polypeptide binds to an MHC class II complex that has been associated with the autoimmune disease.

In another embodiment, the method for treating an autoimmune disease in a mammal further involves inhibiting the proliferation or function of T cells which are responsive to an autoantigen. RA is a T cell-mediated autoimmune disease which can be treated with the present polypeptides. The pathological process of autoimmune diseases and immune rejection is mediated by T cells. Upon binding to and recognition of an antigen, T cells proliferate, secrete cytokines and recruit additional inflammatory and cytotoxic cells to the site. The present polypeptides affect T cell functions such as cytokine secretion and recruitment of inflammatory and cytotoxic cells to the site. When the autoimmune disease is an arthritic condition the autoantigen can be collagen, and the present polypeptides can inhibit the function of collagen-responsive T cells.

In another embodiment, the method for treating an autoimmune disease in a mammal involves binding the polypeptide to an antigen presenting cell such as a macrophage, a dendritic cell of the lymphoid tissue or an epidermal cell. The proliferation and functions of a T cell are activated when an appropriate antigen is presented to it. By binding to antigen presenting cells, the present polypeptides may block or otherwise interfere with T cell activation.

In yet another embodiment, the method for treating an autoimmune disease in a mammal involves binding the polypeptide to a MHC class II complex which is associated with an autoimmune disease. The class II MHC complex is expressed predominantly on the surfaces of B lymphocytes and antigen presenting cells such as macrophages. These Class II MHC complexes have a peptide-binding cleft which is the site at which antigenic peptides are presented to T cells. When the present polypeptides bind to a MHC class II complex, those polypeptides can block or otherwise interfere with antigen presentation and/or T cell activation.

In another embodiment, the method for treating an autoimmune disease in a mammal involves binding the polypeptide to GA-reactive B cell antibodies, and/or GA-reactive T cells. GA-reactive TH2/3 T cells facilitate the therapeutic effects of GA. When binding to GA-reactive T cells, the present polypeptides stimulate those T cells to proliferate, secrete anti-inflammatory cytokines and enhance the therapeutic benefits of treatment by the present methods. According to the present invention, the present polypeptides also bind to autoantigen-reactive antibodies which may block the antibody from attacking the target tissue, thereby helping to prevent the autoimmune disease from progressing.

It should be understood that all combinations of the described embodiments are also within the scope of the invention.

DEFINITIONS

Relapses:

Relapses are characterized by the occurrence of neurological dysfunction symptoms, appearing after a 30-day period of stability or improvement and lasting for more than 24 hours (no infection, no fever). The number of relapses are analyzed using a logistic regression model controlling for treatment and age.

"Relapse Rate" is the number of confirmed relapses per unit time. "Annualized relapse rate" (ARR) is the mean value of the number of confirmed relapses per each patient multiplied by 365 and divided by the number of days on study drug per each patient.

Forms of Multiple Sclerosis:

There are five distinct disease stages and/or types of MS:
1) benign multiple sclerosis;
2) relapsing-remitting multiple sclerosis (RRMS);
3) secondary progressive multiple sclerosis (SPMS);
4) progressive relapsing multiple sclerosis (PRMS; and
5) primary progressive multiple sclerosis (PPMS)

Benign multiple sclerosis is a retrospective diagnosis which is characterized by 1-2 exacerbations with complete recovery, no lasting disability and no disease progression for 10-15 years after the initial onset. Benign multiple sclerosis may, however, progress into other forms of multiple sclerosis.

Patients suffering from RRMS experience sporadic exacerbations or relapses, as well as periods of remission. Lesions and evidence of axonal loss may or may not be visible on MRI for patients with RRMS.

SPMS may evolve from RRMS. Patients afflicted with SPMS have relapses, a diminishing degree of recovery during remissions, less frequent remissions and more pronounced neurological deficits than RRMS patients. Enlarged ventricles, which are markers for atrophy of the corpus callosum, midline center and spinal cord, are visible on MRI of patients with SPMS.

PPMS is characterized by a steady progression of increasing neurological deficits without distinct attacks or remissions. Cerebral lesions, diffuse spinal cord damage and evidence of axonal loss are evident on the MRI of patients with PPMS. PPMS has periods of acute exacerbations while proceeding along a course of increasing neurological deficits without remissions. Lesions are evident on MRI of patients suffering from PRMS. (28)

A clinically isolated syndrome (CIS) is a single monosymptomatic attack compatible with MS, such as optic neuritis, brain stem symptoms, and partial myelitis. Patients with CIS that experience a second clinical attack are generally considered to have clinically definite multiple sclerosis (CDMS). Over 80 percent of patients with a CIS and MRI lesions go on to develop MS, while approximately 20 percent have a self-limited process. (29, 30)

Multiple sclerosis may present with optic neuritis, blurring of vision, diplopia, involuntary rapid eye movement, blindness, loss of balance, tremors, ataxia, vertigo, clumsiness of a limb, lack of co-ordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning.

Relapsing Form of Multiple Sclerosis:

The term relapsing MS includes:
1) patients with RRMS;
2) patients with SPMS and superimposed relapses; and
3) patients with CIS who show lesion dissemination on subsequent MRI scans according to McDonald's criteria.

As used herein, relapsing forms of multiple sclerosis include: Relapsing-remitting multiple sclerosis (RRMS), characterized by unpredictable acute episodes of neurological dysfunction (relapses), followed by variable recovery and periods of clinical stability;

Secondary Progressive MS (SPMS), wherein patients having RRMS develop sustained deterioration with or without relapses superimposed; and Primary progressive-relapsing multiple sclerosis (PPRMS) or progressive-relapsing multiple sclerosis (PRMS), an uncommon form wherein patients developing a progressive deterioration from the beginning can also develop relapses later on.

As used herein, a responder (R) is a patient with an annual relapse rate (ARR)<0.5 and no evidence of disease progression as measured by EDSS (expanded disability status scale). A hypo/non-responder (HR/NR) is a patient with an ARR>0.5 and/or with progression in the EDSS of at least 1 point sustained for 6 months Kurtzke Expanded Disability Status Scale (EDSS):

The Kurtzke Expanded Disability Status Scale (EDSS) is a method of quantifying disability in multiple sclerosis. The EDSS replaced the previous Disability Status Scales which used to bunch people with MS in the lower brackets. The EDSS quantifies disability in eight Functional Systems (FS) and allows neurologists to assign a Functional System Score (FSS) in each of these. The Functional Systems are: pyramidal, cerebellar, brainstem, sensory, bowel and bladder, visual & cerebral (according to www.mult-sclerosis.org/expandeddisabilitystatusacale).

As used herein, "modifying treatment" includes stopping administration of a pharmaceutical composition, stopping administration of the pharmaceutical composition in favor of an alternative treatment, adding a further treatment to be used in conjunction with the pharmaceutical composition, changing the dose of the pharmaceutical composition, or any combination thereof.

As used herein, "in the blood of the subject" is represented by "serum," PBMCs derived from the subject's blood, and also the "supernatant" of PBMCs derived from the subject's blood.

As used herein "3 months" refers to a time point which is three months after the beginning of administration of a pharmaceutical composition to a subject. "6 months" refers to a time point which is six months after the beginning of administration of a pharmaceutical composition to a subject.

As used herein, the "supernatant" at "3 months" or the "supernatant" at "6 months" refers to supernatants collected from Peripheral blood mononuclear cells (PBMCs) purified from subject blood samples taken at 3 months or at 6 months and incubated in the presence or absence of antigen, e.g., glatiramer acetate, as described in the methods hereinbelow.

As used herein, "unstimulated IL-4/IFN-γ ratio" refers to a IL-4/IFN-γ ratio value measured in the blood of a subject where the blood of the subject, or PBMCs derived from the blood of the subject, has not been incubated in the presence of an antigen.

As used herein, a "reference value" is a value measured before the beginning of administration of a pharmaceutical composition to a subject afflicted with an autoimmune disease, or a value which has previously been determined to be associated with a response or non-response to a treatment for the autoimmune disease, where the treatment comprises administration of the pharmaceutical composition or comprises administration of a different pharmaceutical composition.

For the purpose of the present invention, "glatiramer acetate or a glatiramer acetate-related peptide or polypeptide" is intended to include any peptide or polypeptide, including a random copolymer, that cross-reacts functionally with myelin basic protein (MBP) and is able to compete with MBP on binding to the MHC class II in the antigen presentation.

A copolymer for use as active agent in the present invention may be a random copolymer comprising a suitable quantity of a positively charged amino acid such as lysine (K) or arginine (R), in combination with a negatively charged amino acid (preferably in a lesser quantity) such as glutamic acid (E) or aspartic acid (D), optionally in combination with a non-charged neutral amino acid such as alanine (A) or glycine (G), serving as a filler, and optionally with an amino acid adapted to confer on the copolymer immunogenic properties, such as an aromatic amino acid like tyrosine (Y) or tryptophan (W).

The copolymers for use in the present invention can be composed of L- or D-amino acids or mixtures thereof. As is known by those of skill in the art, L-amino acids occur in most natural proteins. However, D-amino acids are commercially available and can be substituted for some or all of the amino acids used to make the copolymers used in the present invention. The present invention contemplates the use of copolymers containing both D- and L-amino acids, as well as copolymers consisting essentially of either L- or D-amino acids.

In one embodiment, the active agent for use in the present invention comprises at least one random three- or four-amino acid copolymer comprising one amino acid selected from each of the four following groups: (a) lysine (K) and arginine (R); (b) glutamic acid (E) and aspartic acid (D); (c) alanine (A) and glycine (G); and (d) tyrosine (Y) and tryptophan (W).

In one embodiment, the copolymer comprises a combination of the amino acids tyrosine, glutamic acid, alanine, and lysine, herein designated poly-YEAK, of net overall positive electrical charge. In an embodiment, the copolymer is GA, of the following molar ratio of the amino acids: about 0.14 glutamic acid, about 0.43 alanine, about 0.10 tyrosine, and about 0.34 lysine. It may be a low molecular weight or high molecular weight copolymer being a polypeptide from about 15 to about 100, preferably from about 40 to about 80, amino acids in length. The copolymer has an average molecular weight of about 2,000-40,000 Da, preferably of about 2,000-13,000 Da, more preferably of about 4,700-13,000 Da, most preferably of about 5,000-9,000 Da, and mostly preferred of about 6,000-8,000 Da. Preferred molecular weight ranges and processes for making a preferred form of GA are described in U.S. Pat. No. 5,800,808, the entire contents of which is hereby incorporated by reference in its entirety as if fully disclosed herein.

It is clear that this is given by way of example only, and that the active agent can be varied both with respect to the constituents and relative proportions of the constituents, thus obtaining poly-YEAK copolymers different from GA.

In another embodiment, the active agent of the present invention is a GA-related polypeptide that is a random copolymer containing four different amino acids, each from a different one of the groups (a) to (d), but excluding GA. The activity exhibited by GA is expected to remain if one or more of the following substitutions is made in the amino acid composition of the copolymer: aspartic acid (D) for glutamic acid (E), glycine (G) for alanine (A), arginine (R) for lysine (K), and tryptophan (W) for tyrosine (Y).

Thus, in another embodiment, the GA-related polypeptide of the invention may include any of those copolymers disclosed in WO 00/05250, the entire contents of which is hereby incorporated herein by reference as if fully disclosed herein, and other synthetic amino acid copolymers such as the random four-amino acid copolymers described by Fridkis-Hareli et al. (31) as candidates for treatment of multiple sclerosis, namely copolymers (14-, 35- and 50-mers) containing the amino acids phenylalanine, glutamic acid, alanine and lysine (poly-FEAK), or tyrosine, phenylalanine, alanine and lysine (poly-YFAK), and any other similar copolymer to be discovered that can be considered a universal antigen similar to GA.

In another embodiment, the GA-related polypeptide of the invention is a copolymer containing a combination of three different amino acids each from a different one of three groups of the groups (a) to (d). These copolymers are herein referred to as terpolymers. In an embodiment, the mole fraction of amino acids of the terpolymers is about what is preferred for GA.

In one embodiment, the terpolymers for use in the present invention contain tyrosine (Y), alanine (A), and lysine (K), hereinafter designated poly-YAK. The average molar fraction of the amino acids in these terpolymers can vary. For example, tyrosine can be present in a mole fraction of about 0.005-0.250; alanine can be present in a mole fraction of about 0.3-0.6; and lysine can be present in a mole fraction of about 0.1-0.5, but preferably the molar ratios of tyrosine, alanine and lysine are about 0.10 to about 0.54 to about 0.35. The average molecular weight of poly-YAK is about 2,000-40,000 Da, preferably about 3,000-35,000 Da, more preferably about 5,000-25,000 Da. It is possible to substitute arginine (R) for lysine (K), glycine (G) for alanine (A), and or tryptophan (W) for tyrosine (Y).

In another embodiment, the terpolymers for use in the present invention contain tyrosine (Y), glutamic acid (E), and lysine (K), hereinafter designated poly-YEK. The average mole fraction of the amino acids in these terpolymers can vary: glutamic acid can be present in a mole fraction of about 0.005-0.300, tyrosine can be present in a mole fraction of about 0.005-0.250, and lysine can be present in a mole fraction of about 0.3-0.7, but preferably the molar ratios of glutamic acid, tyrosine, and lysine are about 0.26 to about 0.16 to about 0.58. The average molecular weight of poly-YEK is about 2,000-40,000 Da, preferably about 3,000-35,000 Da, more preferably about 5,000-25,000 Da. It is possible to substitute arginine (R) for lysine (K), aspartic acid (D) for glutamic acid (E), and/or tryptophan (W) for tyrosine (Y).

In a further embodiment, the terpolymers for use in the present invention contain lysine (K), glutamic acid (E), and alanine (A), hereinafter designated poly-KEA. The average molar fraction of the amino acids in these polypeptides can also vary. For example, glutamic acid can be present in a mole fraction of about 0.005-0.300, alanine in a mole fraction of about 0.005-0.600, and lysine can be present in a mole fraction of about 0.2-0.7, but preferably the molar ratios of glutamic acid, alanine and lysine are about 0.15 to about 0.48 to about 0.36. The average molecular weight of YEK is about 2,000-40,000 Da, preferably about 3,000-35,000 Da, more preferably about 5,000-25,000 Da. It is possible to substitute arginine (R) for lysine (K), aspartic acid (D) for glutamic acid (E), and/or glycine (G) for alanine (A).

In still another embodiment, the terpolymers for use in the present invention contain tyrosine (Y), glutamic acid (E), and alanine (A), hereinafter designated poly-YEA. The average molar fraction of the amino acids in these polypeptides can vary. For example, tyrosine can be present in a mole fraction of about 0.005-0.250, glutamic acid can be present in a mole fraction of about 0.005-0.300, and alanine can be present in a mole fraction of about 0.005-0.800, but preferably the molar ratios of glutamic acid, alanine, and tyrosine are about 0.21 to about 0.65 to about 0.14. The average molecular weight of poly-YEA is about 2,000-40,000 Da, preferably about 3,000-35,000 Da, and more preferably about 5,000-25,000 Da. It is possible to substitute tryptophan (W) for tyrosine (Y), aspartic acid (D) for glutamic acid (E), and/or glycine (G) for alanine (A).

The terpolymers can be made by any procedure available to one of skill in the art for example as described in publications WO 01152878 and WO 01/93893, the entire contents of which are hereby incorporated by reference in their entirety.

As binding motifs of GA to MS-associated HLA-DR molecules are known, polypeptides of fixed sequence can readily be prepared and tested for binding to the peptide-binding groove of the HLA-DR molecules as described in Fridkis-Hareli et al. (32) Examples of such peptides are those disclosed in WO 005249, the entire contents of which are hereby incorporated by reference as if fully disclosed herein.

Example 1

Evaluating Predictive Value of Clinical Response to GA in Patients Classified as GA-R or GA-HR/NR This is a prospective study in which sixty-two relapsing-remitting MS (RR-MS) patients treated with GA were classified clinically as GA-R (N=42) or GA-HR/NR (N=20) after 2 years of treatment. Cytokine levels, brain-derived neurotrophic factor (BDNF) levels, and T-cell proliferation to GA were analyzed at baseline, 3, 6, 9-12 and 24 months and assessed for their predictive value of clinical response after 2 years of treatment.

Methods

Subjects

Sixty-two patients diagnosed with definite RR-MS (relapsing-remitting MS) according to the McDonald criteria (33) were included in the study. Following recruitment, the patients were treated with GA for at least 2 years. Subjects were closely followed up at the University of Medicine and Dentistry New Jersey (UMDNJ)-Robert Wood Johnson Medical School, University of Maryland Center for MS, the Gimbel MS Center, Teaneck, N.J. and the Carolina Medical Center-MS Center, Charlotte, N.C. The clinical characteristics of the patients are presented in Table 1. Fifty patients were females with a mean age of 41±10.3 years and 12 were males with a mean age of 39.0±11.9 years. Patients had at least one relapse during the year prior to initiation of GA therapy (Table 2). After at least 2 years on GA therapy, patients were classified as GA-R (n=42) or GA-HR/NR (n=20) based on a clinical criteria more stringent than those recently reported in the literature. (34) A responder (R) is a patient with an annual relapse rate (ARR)<0.5 and no evidence of disease progression as measured by EDSS (expanded disability status scale). A hypo/non-responder (HR/NR) is a patient with an ARR>0.5 and/or with progression in the EDSS of at least 1 point sustained for 6 months (Table 3).

TABLE 1

Characteristics of MS patients and their clinical classification

| ID No | Age/Sex | Disease Duration (yrs) | Treatment Duration (mo) | EDSS Pre-Rx | EDSS On-Rx | ARR Pre-Rx | ARR On-Rx | Clinical Status |
|---|---|---|---|---|---|---|---|---|
| 1. G1 | 35/M | 6 | 24 | 2.5 | 0 | 0.5 | 0 | R |
| 2. G2 | 47/F | 18 | 24 | 3 | 2 | 0.5 | 0 | R |
| 3. G4 | 53/F | 28 | 24 | 3 | 1 | 0.5 | 0 | R |
| 4. G5 | 29/F | 8 | 24 | 2 | 3 | 2.0 | 2 | HR/NR |
| 5. G6 | 59/F | 15 | 24 | 2.5 | 2.5 | 0.5 | 1 | HR/NR |
| 6. G8 | 53/F | 2 | 24 | 2 | 2 | 0.5 | 0 | R |
| 7. G9 | 52/F | 6 | 24 | 1 | 2 | 0.5 | 0.5 | HR/NR |
| 8. N1 | 34/F | 9 | 24 | 2.5 | 2.5 | 1 | 0.5 | R |
| 9. N2 | 31/F | 6 | 24 | 3.5 | 2.5 | 0.5 | 0 | R |
| 10. N3 | 38/F | 4 | 24 | 2.5 | 3.5 | 1.5 | 0.5 | HR/NR |
| 11. N4 | 28/F | 6 | 24 | 2.5 | 2 | 0.5 | 0 | R |
| 12. N5 | 49/F | 5 | 24 | 2.5 | 1.5 | 1.5 | 0 | R |
| 13. N6 | 40/F | 16 | 24 | 6 | 6 | 0 | 0 | R |
| 14. N7 | 42/F | 5 | 24 | 2.5 | 1 | 1 | 0 | R |
| 15. N9 | 27/M | 6 | 24 | 3.5 | | 1 | | R |
| 16. N10 | 37/M | 6 | 24 | 3 | 4 | 0.5 | 0 | HR/NR |
| 17. N11 | 40/M | 10 | 24 | 2 | 3 | 1 | 0.5 | HR/NR |
| 18. N12 | 42/F | 3 | 24 | 2.5 | 2 | 1 | 0.5 | R |
| 19. N13 | 33/M | 5 | 24 | 1 | 1 | 0.5 | 0 | R |
| 20. N14 | 49/F | 18 | 24 | 4 | 6 | 1 | 0 | HR/HR |
| 21. N15 | 53/F | 12 | 24 | 1.5 | 2.5 | 0 | 0 | HR/NR |
| 22. N16 | 33/M | 9 | 24 | 1 | 0 | 0 | 0 | R |
| 23. N17 | 24/M | 7 | 24 | 4 | 2 | 1 | 0 | R |
| 24. N18 | 17/F | 4 | 24 | 1.5 | 1.5 | 1 | 0.5 | R |
| 25. N19 | 37/F | 5 | 24 | 2.5 | 2 | 0 | 0 | R |
| 26. N20 | 46/F | 18 | 24 | 2 | 4 | 1 | 1 | HR/NR |
| 27. N21 | 31/F | 9 | 24 | 1 | 0 | 0 | 0.5 | R |
| 28. C1 | 32/F | 5 | 36 | 2 | 1.5 | 0 | 0 | R |
| 29. C2 | 45/M | 6 | 24 | 2 | 2.5 | 0.5 | 1 | HR/HR |
| 30. C3 | 45/F | 23 | 24 | 1.5 | 1.5 | 2 | 0 | R |
| 31. C4 | 32/F | 3 | 24 | 3.5 | 1.5 | 1 | 0.5 | R |
| 32. C5 | 29/F | 4 | 24 | 1 | 0 | 1 | 0.5 | R |
| 33. C6 | 60/F | 5 | 48 | 5 | 1.5 | 1 | 0 | R |
| 34. C7 | 53/F | 8 | 24 | 1.5 | 5 | 0.5 | 0.5 | HR/NR |
| 35. C8 | 53/F | 21 | 24 | 2 | 1.5 | 0 | 0 | R |
| 36. C10 | 43/F | 13 | 36 | 2 | 2 | 1 | 1 | HR/NR |
| 37. C11 | 52/F | 25 | 24 | 2 | 5 | 1.5 | 0 | HR/NR |
| 38. C12 | 40/F | 12 | 24 | 1.5 | 2 | 0 | 0 | R |
| 39. C13 | 44/F | 16 | 48 | 1.5 | 1.5 | 1 | 0 | R |
| 40. C14 | 51/F | 3 | 48 | 1.5 | 2.5 | 1 | 1 | HR/NR |
| 41. C15 | 51/F | 20 | 38 | 1.5 | 1.5 | 1 | 1 | R |
| 42. C16 | 40/M | 16 | 24 | 0 | 1.5 | 0 | 0.5 | HR/NR |
| 43. C17 | 60/M | 5 | 30 | 1.5 | 2 | 1 | 1.5 | HR/NR |
| 44. C18 | 29/F | 5 | 25 | 2 | 2 | 1 | 0 | R |
| 45. C19 | 22/F | 2 | 24 | 2 | 0 | 0 | 0 | R |
| 46. C20 | 53/F | 32 | 24 | 4 | 5 | 0.5 | 0.5 | HR/NR |
| 47. C21 | 49/F | 5 | 24 | 2 | 2 | 1 | 0 | R |
| 48. C22 | 63/M | 6 | 27 | 2.5 | 2.5 | 0 | 0 | R |
| 49. C23 | 39/F | 5 | 24 | 1 | 2 | 0.5 | 0.5 | HR/NR |
| 50. C24 | 36/F | 8 | 24 | 1.5 | 1.5 | 1 | 0 | R |
| 51. C25 | 28/F | 7 | 24 | 2.5 | 1.5 | 0.5 | 0.5 | R |
| 52. C26 | 36/F | 6 | 24 | 1.5 | 2 | 0.5 | 0.5 | R |
| 53. C27 | 32/F | 5 | 24 | 2 | 3 | 0.5 | 1 | HR/NR |
| 54. C28 | 30/F | 3 | 24 | 2 | 2 | 0.5 | 0.5 | R |
| 55. U4 | 40/F | 12 | 48 | 2 | 2 | 1 | 0.5 | R |
| 56. U9 | 53/F | 25 | 24 | 1 | 2 | 1 | 1.5 | HR/NR |
| 57. U10 | 50/F | 4 | 24 | 2 | 1 | 1 | 0 | R |
| 58. U13 | 44/F | 7 | 24 | 1 | 1 | 1 | 0 | R |
| 59. U17 | 38/F | 7 | 24 | 1 | 1 | 1 | 0 | R |
| 60. U20 | 32/M | 8 | 24 | 1 | 1 | 0.5 | 0 | R |

TABLE 1-continued

Characteristics of MS patients and their clinical classification

| ID No | Age/Sex | Disease Duration (yrs) | Treatment Duration (mo) | EDSS Pre-Rx | EDSS On-Rx | ARR Pre-Rx | ARR On-Rx | Clinical Status |
|---|---|---|---|---|---|---|---|---|
| 61. U21 | 27/F | 2 | 24 | 1 | 1 | 0.5 | 0 | R |
| 62. U22 | 31/F | 10 | 24 | 2 | 1 | 0.5 | 0 | R |

ARR: Annual Relapse Rate
EDSS: Expanded Disability Status Scale
R: Clinical Responder
HR/NR: clinical Hypo/Non-Responder
Rx: Treatment
G: MS Center at Holy Name Hospital Patients
N: Carolina Medical Center, MS Center Patients
C: University of Maryland, MS Center Patients
U: UMDNJ-RWJH MS Center Patients

TABLE 2

Patients Demographics

| Demographics | GA-R | GA-HR/NR | p values |
|---|---|---|---|
| Number of patients | 42 | 20 | |
| Mean Age | 38 ± 10.4 | 46.2 ± 8.9 | NS |
| Sex | | | |
| M | 7 | 5 | |
| F | 35 | 15 | |
| Mean Duration of illness (years) | 8.3 ± 6.1 | 12.2 ± 8.2 | NS |
| Mean ARR | | | |
| Pre-Rx | 0.67 ± 0.46 | 0.80 ± 0.49 | NS |
| 24 mo Rx | 0.14 ± 0.25 | 0.75 ± 0.50 | 0.03 |
| Mean EDSS | | | |
| Pre-Rx | 2.18 ± 1.08 | 1.95 ± 0.95 | NS |
| 24 mo Rx | 1.57 ± 1.0 | 3.2 ± 1.37 | <0.01 |

R: Responder
HR/NR: Hypo/Non-responder
*NS: not significant

TABLE 3

Criteria for clinical classification after 2 years of treatment with GA.

| GA-R (N = 42) | GA-HR/NR (N = 20) |
|---|---|
| Annual Relapse Rate <0.5 and No evidence of sustained disease progression as measured by EDSS | Annual Relapse Rate >0.5 and/or Progression in the EDSS of at least 1 point sustained for ≥6 months |

R: Responder;
HR/NR: Hypo/Non-responder

Cells

Approximately 60 cc of blood was obtained by venipuncture from each MS patient pre-treatment and at successive time points during treatment (3 months, 6 months, 9-12 months and 24 months). PBMC were purified using Ficoll-Hypaque gradients as described in the supplier's protocol (ICN Biomedicals Inc. Ohio, USA). Samples from collaborating centers were sent via overnight FedEx™ delivery at room temperature and processed immediately upon arrival.

Lymphoproliferation Assay $2 \times 10^5$ PBMC/well were seeded in 96 well U-bottom micro titer plate in the absence of antigen (unstimulated condition) (US) or the presence of GA at 40 and 100 μg/ml (Teva Pharmaceutical Industries, Ltd., Israel), tetanus toxoid (TT 5 μg) obtained from UMASS (University of Mass, Worcester, Mass.). The latter was used as a control antigen. Supernatants were collected from cultured cells at days 1, 3 and 5 for various assays. After 5 days, 1 μCi $^3$H-thymidine was added. Cells were harvested 18 hours later using TOMTEC cell harvester (TOMTEC, Hamden Conn.). Incorporated radioactivity was measured using a liquid Scintillation counter (Wallac MicroBeta Trilux, PerkinElmer, Boston, Mass.).

ELISPOT Assay

Human IFN-γ (Th1 indicator) and IL-4 (Th2 indicator) were measured by the ELISPOT assay according to the manufacturer's protocol (BD Biosciences, San Diego, Calif., USA). Briefly, ELISPOT plates (PVDF plate, Millipore Corporation, MA, USA) were coated with 100 μl/well of 5 μg/ml capture antibody at 4° C. over night. The plates were then washed with PBS, and incubated with 200 μl/well of blocking solution (culture medium) for 2 hours. PBMC ($2 \times 10^5$ cells/well for IFN-γ and $4 \times 10^5$ cells/well for IL-4 detection) and antigen (GA 40 and 100 μg/ml, TT 5 μg/ml, CD3Ab (2.5 μg/ml)/CD28 Ab (1 μg/ml)) was added and cultured overnight at 37° C. in a 5% $CO_2$ incubator. Samples were tested in triplicate wells in response to each antigen. After overnight culture, the plates were washed twice with deionized water and three times with PBS, then incubated with 100 μl of 2.0 μg/ml biotinylated antibody for 2 hours at room temperature. The plates were then washed three times with wash buffer (0.05% Tween-20 PBS), and incubated with 100 μl of 1:100 dilution of Avidin-HRP for 1 hour at room temperature and washed three times with wash buffer. Finally 100 μl of AEC (3-amino-9-ethyl-carbazole) substrate was added and the reaction was stopped by washing plates with distilled water. Spots were counted and analyzed by CTL Analyzers LLC ELISPOT Plate Reader (Cleveland, Ohio, USA).

ELISA

Interleukin-18 and caspase-1 levels were detected by human ELISA kits (Sandwich ELISA, Bender Nedaystems, USA). The sensitivity of the ELISA was 9.2 and 3.3 pg/ml for IL-18 and caspase-1 respectively. TGF-β, TNF-α, IL-4, IFN-γ, IL-17 and IL-10 levels were detected by human ELISA kits from ebioscience (San Diego Calif., 92121 USA). The sensitivity of the ebioscience kits were 60 pg/ml, 4 pg/ml, 2 pg/ml, 4 pg/ml, 4 pg/ml and 2 pg/ml respectively. BDNF was detected by the Human BDNF ELISA kit from Chemicon International (catalog #CYT306). The sensitivity of the BDNF ELISA was 7.8 pg/ml. According to assay instructions, the limit of detection of the cytokines was defined as the analyte concentration resulting in an absorption significantly higher than that of the dilution medium (calculated as the mean plus 2 standard deviations). Duplicates should be within 20% of the mean.

Statistical Analysis

A software package (Graphpad, Prism 5.0™) was used in the statistical analysis. The differences between GA-R and GA-HR/NR were compared using ANOVA, paired or unpaired t-test as well as Bonferroni's test for multiple column analysis. A p-value <0.05 was considered statistically significant. Results are expressed as mean±SD or mean±SEM.

Results

Classification of Clinical Responders and Hypo/Non-Responders

The patients were classified as GA-responders or hypo/non-responders after being treated with GA for at least 24 months, based on their ARR and progression in disability while on treatment (Tables 1 and 3). The mean disease duration was 8.3±6.1 years for the GA-R group and 12.2±8.2 years for GA-HR/NR group. The mean treatment duration was 26.4±6.6 months for the GA-R group and 26.1±5.9 months for the GA-HR/NR group. The baseline ARR and EDSS were not significantly different between the GA-R and the GA-HR/NR groups. However, the ARR and EDSS were significantly lower at the end of the treatment period in the GA-R group compared to the GA-HR/NR. Overall, a 79% reduction in the ARR and a 0.61 point decrease in the EDSS occurred in the GA-R, whereas a 6.25% reduction in the ARR and a 1.12 point increase in the EDSS occurred in the GA-HR/NR during treatment (Table 2).

Lymphoproliferative Response

The ex-vivo PBMC proliferative response to GA and TT are presented in FIG. 1 as ΔCPM (mean cpm in antigen stimulated minus mean cpm in unstimulated wells). The background activity (unstimulated condition) mean range was 190-700 CPM. Overall, there was an initial increase in the proliferative response to GA and TT at 3 months during treatment followed by a decline after 6 months of treatment. There was no difference in PBMC proliferation to GA or TT between GA-R and GA-HR/NR before or during treatment at 3, 6, 12 months or 2 years (p values at all time points were >0.05).

Cytokine Expression

Figure 2A:
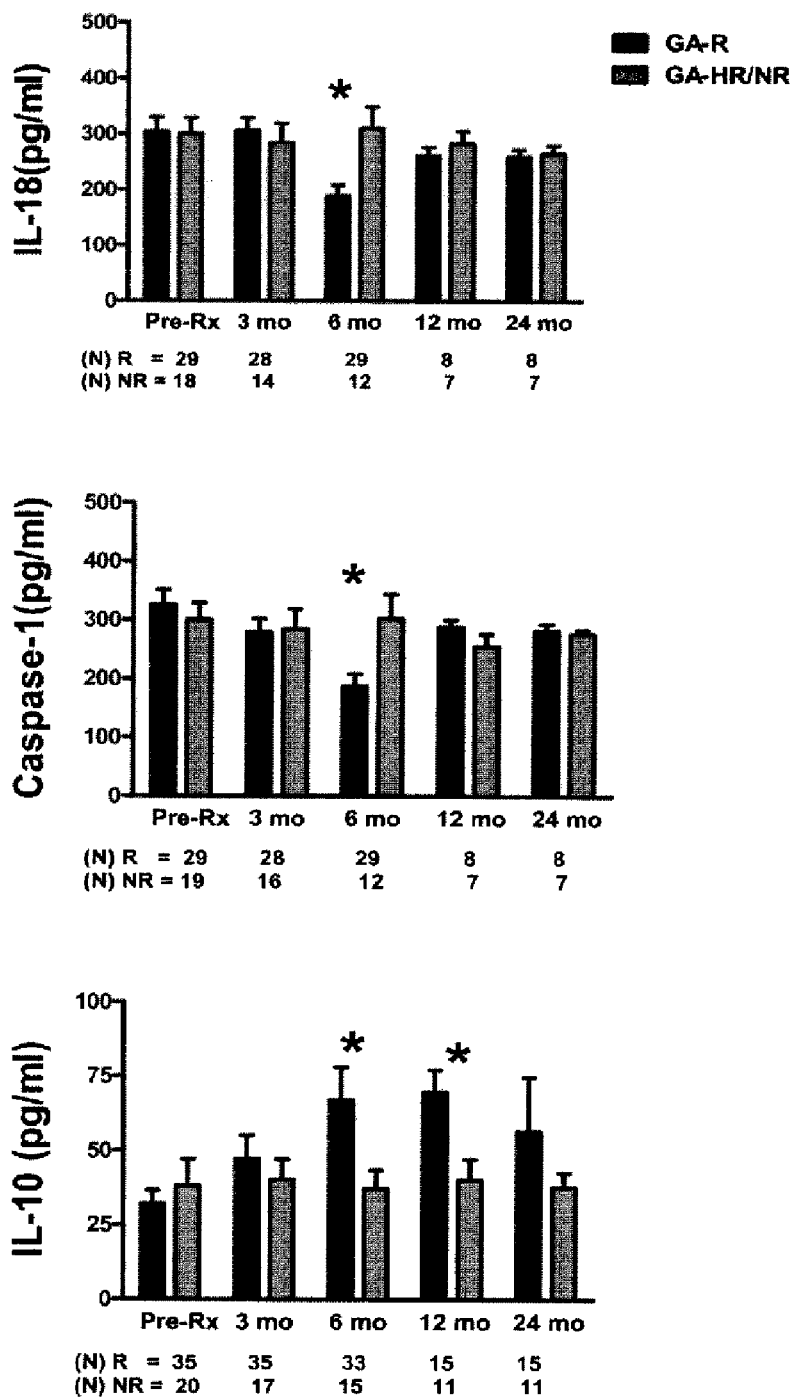
Figure 2B:
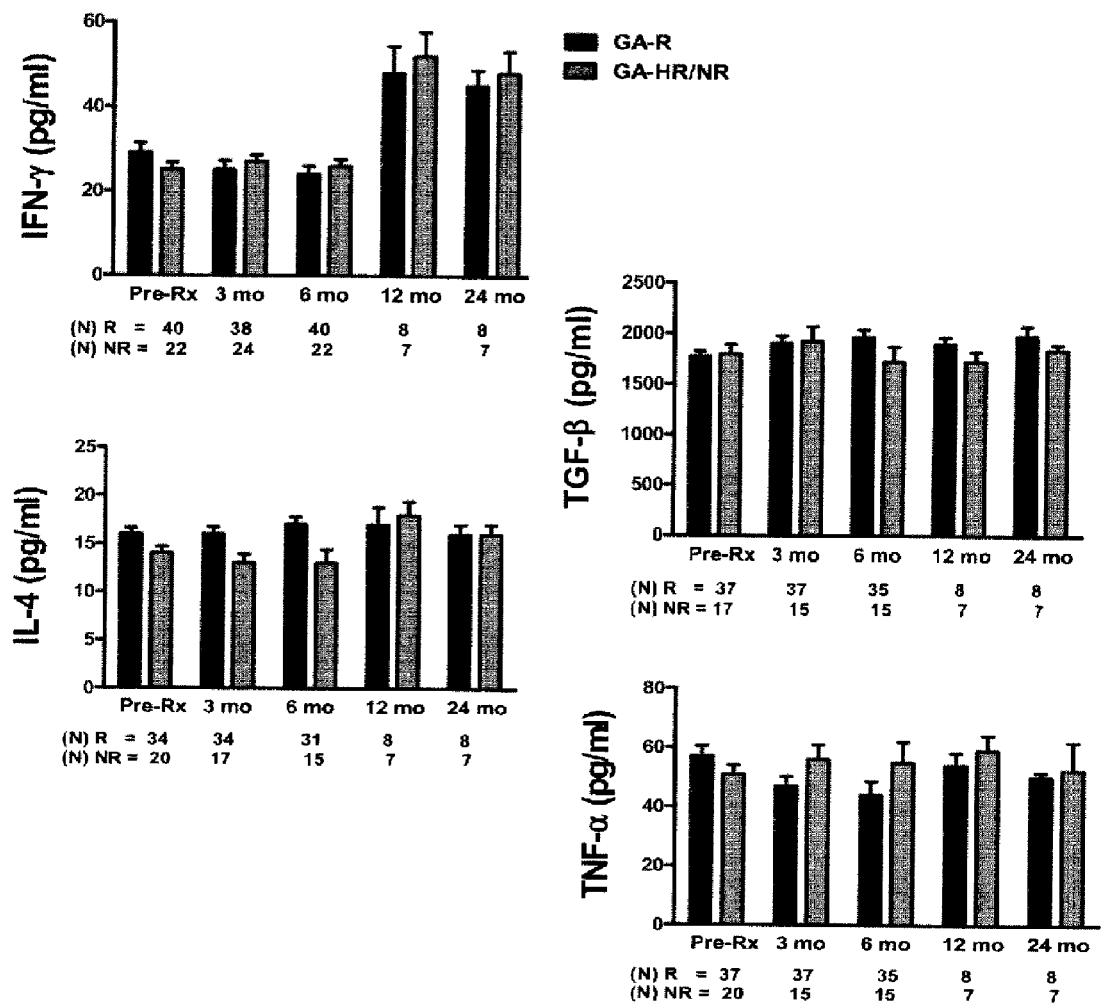
Figure 3A:
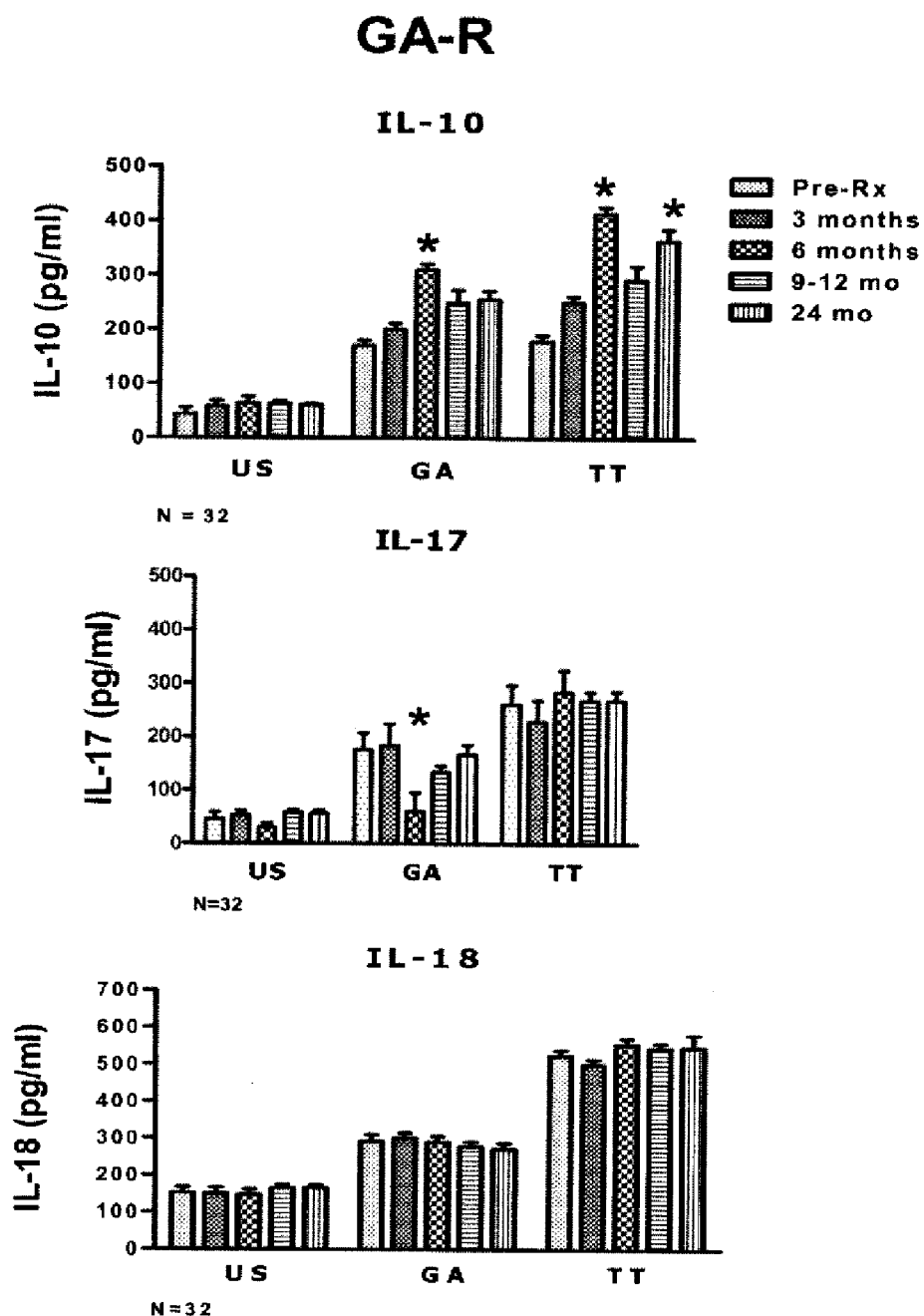
Figure 3B:
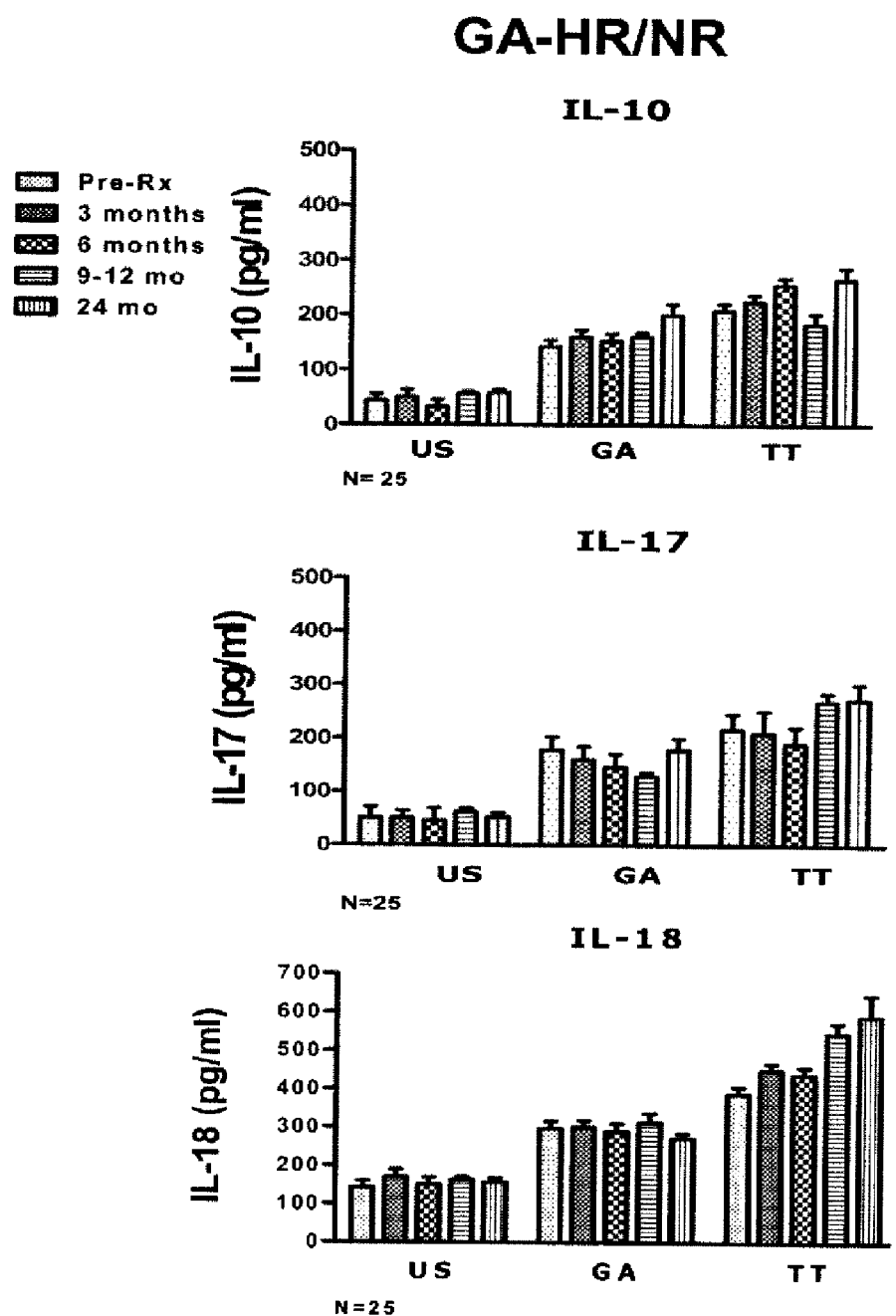

Cytokine levels in serum and supernatant at different time points from the GA-R and the GA-HR/NR are shown in Table 4. Serum IL-18 levels were significantly decreased among GA-R during GA treatment compared to pre-treatment only at month 6 ($p=0.017$), while the reduction in IL-18 was not significant among GA-HR/NR at any time point ($p>0.05$) (FIG. 2). Supernatant IL-18 levels did not show any significant changes from baseline and did not differ between the 2 groups (FIG. 3). Since caspase-1 regulates IL-18 secretion by proteolytic cleavage of the immature IL-18 (35), we measured caspase-1 levels, which were significantly reduced during treatment among GA-R ($p=0.04$) but was unchanged among GA-HR/NR ($p>0.05$). Glatiramer acetate treatment resulted in an increase in IL-10 levels during the course of treatment in both serum and PBMC supernatants during therapy compared to pre-treatment levels. Although serum and supernatant IL-10 levels showed an increase as early as 3 months during treatment, such an increase became statistically significant at 6 months ($p=0.011$ and $0.01$) (FIGS. 2 and 3). Compared to baseline, supernatants from ex-vivo GA-stimulated cells showed a reduction in IL-17 levels in the GA-R but not the HR/NR. The reduction in IL-17 was only significant at 6 months during treatment ($p<0.01$) (FIG. 3). No significant changes from baseline or differences between GA-R and GA-HR/NR for IFN-γ, TNF-α, TGF-β, and IL-4 serum levels were seen when measured by ELISA (FIG. 2 and Table 4).

Figure 4:
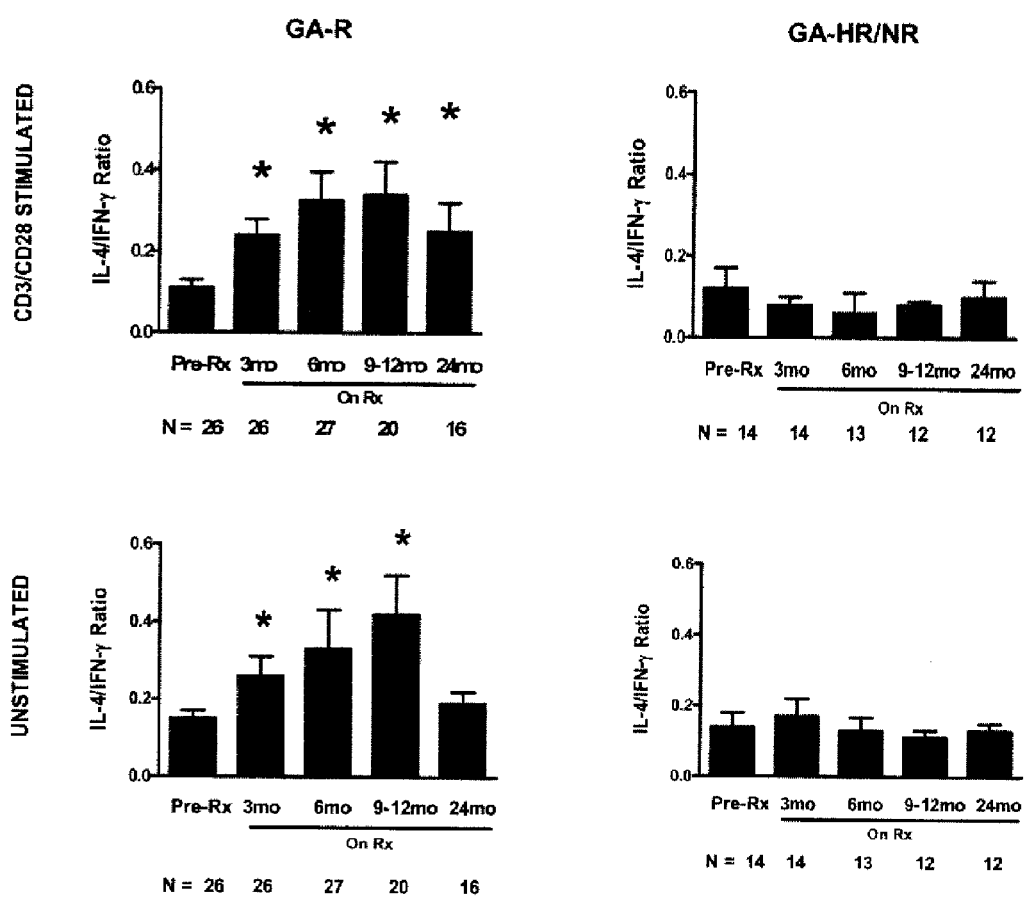

Since ELISA failed to demonstrate differences in IFN-γ and IL-4 levels between GA-R and GA-HR/NR, we employed a more sensitive assay (ELISPOT) for measuring these cytokines. Expression of IFN-γ and IL-4 examined by ELISPOT in PBMC obtained ex-vivo from GA-treated MS patients at baseline and at various time points during treatment are presented in Table 5. The mean number of IFN-γ spots in anti-CD3/CD28 stimulated PBMC declined overtime and was significantly lower at months 12 and 24 compared to baseline in the GA-R group (12 mo $p=0.03$; 24 mo $p=0.01$). This was not observed in the GA-HR/NR group. In contrast, a decline in IL-4 and a stable IFN-γ expression were observed in the GA-HR/NR group. The IL-4/IFN-γ ratio in unstimulated and in anti-CD3/CD28 stimulated PBMC was significantly higher among GA-R during treatment compared to pre-treatment levels (FIG. 4).

Brain-Derived Neurotrophic Factor (BDNF) Expression

Glatiramer acetate stimulated PBMC have been shown to produce BDNF in mice and human. Therefore, we examined the possibility that BDNF expression in PBMC from GA-treated patients may correlate with the clinical response to GA.

Serum BDNF levels did not show significant changes during treatment from baseline in either group nor was there a difference between the two groups at all treatment time points (FIG. 5A). However, supernatant BDNF levels from GA-stimulated PBMCs showed a significant increase at 3 months during treatment compared to baseline in the GA-R group ($p=0.01$), but not in the GA HR/NR group (FIGS. 5 B and C).

TABLE 4

Cytokine levels (pg/ml) in serum and supernatant among GA-R and GA-HR/NR during the course of treatment

| CYTOKINE | PATIENT CLINICAL STATUS | TIME POINT (months) | | | | |
|---|---|---|---|---|---|---|
| | | Pre-Rx | 3 mo | 6 mo | 9-12 mo | 24 mo |
| SERUM | | | | | | |
| IL-18 | R | 304 ± 26 (n = 29) | 279 ± 23 (n = 28) | 189 ± 26 (n = 29) | 262 ± 15 (n = 8) | 260 ± 12 (n = 8) |
| | HR/NR | 300 ± 29 (n = 18) | 284 ± 35 (n = 18) | 310 ± 39 (n = 12) | 283 ± 22 (n = 7) | 265 ± 15 (n = 7) |
| CASPASE-1 | R | 325 ± 26 (n = 29) | 279 ± 23 (n = 26) | 187 ± 21 (n = 29) | 288 ± 12 (8) | 282 ± 11 (n = 8) |
| | HR/NR | 300 ± 29 (n = 19) | 284 ± 35 (n = 16) | 302 ± 42 (n = 12) | 255 ± 21 (7) | 276 ± 7 (n = 7) |

TABLE 4-continued

Cytokine levels (pg/ml) in serum and supernatant among GA-R and GA-HR/NR during the course of treatment

| CYTOKINE | PATIENT CLINICAL STATUS | TIME POINT (months) | | | | |
|---|---|---|---|---|---|---|
| | | Pre-Rx | 3 mo | 6 mo | 9-12 mo | 24 mo |
| IL-10 | R | 32 ± 4.5 (n = 35) | 47 ± 8.1 (n = 35) | 67 ± 11 (n = 33) | 69.8± (n = 15) | 56 ± 18 (n = 15) |
| | HR/NR | 38 ± 9 (n = 20) | 40 ± 7.0 (n = 17) | 37 ± 8.3 (n = 15) | 40 ± 7.0 (n = 11) | 37.6 ± 5 (n = 11) |
| IFN-γ | R | 29 ± 2.3 (n = 40) | 25 ± 2.1 (n = 38) | 24 ± 1.9 (n = 40) | 48 ± 6.3 (n = 8) | 45 ± 3.8 (n = 8) |
| | HR/NR | 25 ± 1.7 (n = 22) | 27 ± 1.45 (n = 24) | 26 ± 1.53 (n = 22) | 52 ± 5.8 (n = 7) | 45 ± 5.3 (n = 7) |
| IL-4 | R | 16 ± 0.60 (n = 34) | 16 ± 0.70 (n = 34) | 17 ± 0.81 (n = 31) | 17 ± 1.8 (n = 8) | 16 ± 1.0 (n = 8) |
| | HR/NR | 14 ± 0.70 (n = 20) | 13 ± 0.92 (n = 17) | 13 ± 1.4 (n = 15) | 18 ± 1.4 (7) | 16 ± 1 (n = 7) |
| TGF-β | R | 1774 ± 48 (n = 37) | 1908 ± 70 (n = 37) | 1968 ± 75 (n = 35) | 1901 ± 64 (n = 8) | 1983 ± 93 (n = 8) |
| | HR/NR | 1796 ± 95 (n = 17) | 1921 ± 150 (n = 15) | 1723 ± 147 (n = 15) | 1727 ± 97 (n = 7) | 1844 ± 53 (n = 7) |
| TNF-α | R | 57 ± 3.6 (n = 37) | 47 ± 3.3 (n = 37) | 44 ± 4.6 (n = 35) | 54 ± 4.24 (n = 8) | 50.13 ± 1.5 (n = 8) |
| | HR | 51 ± 3.0 (n = 20) | 56 ± 5.0 (n = 15) | 55 ± 7.0 (n = 15) | 59 ± 5.18 (n = 7) | 52.4 ± 9.64 (n = 7) |
| SUPERNATANT | | | | | | |
| IL-10 | R | 170 ± 60 (n = 32) | 200 ± 65 (n = 32) | 310 ± 64 (n = 32) | 249 ± 70 (n = 8) | 255 ± 45 (n = 8) |
| | HR/NR | 143 ± 61 (n = 25) | 160 ± 65 (n = 25) | 153 ± 69 n = 26) | 181 ± 22 (8) | 200 ± 59 (n = 8) |
| IL-17 | R | 176 ± 31 (n = 32) | 184 ± 40 (n = 32) | 60 ± 35 (n = 32) | 134 ± 12 (n = 8) | 167 ± 18 (n = 8) |
| | HR/NR | 178 ± 25 (n = 25) | 160 ± 25 (n = 25) | 146 ± 25 (n25) | 129 ± 7.3 (n = 7) | 179 ± 21 (n = 7) |

TABLE 5

IL-4 and IFN-γ expression in CD3/CD28 Stimulated PBMC.

| Time point | IFN-γ | | IL-4 | | IL-4/IFN-γ RATIO | |
|---|---|---|---|---|---|---|
| | R | HR/NR | R | HR/NR | R | HR/NR |
| Baseline | 197 ± 28 (n = 27) | 192 ± 26 (n = 14) | 35 ± 5.9 (n = 27) | 39 ± 9 (n = 14) | 0.11 ± 0.02 (n = 27) | 0.12 ± 0.05 (n = 14) |
| 3 mo | 182 ± 18 (n = 27) | 206 ± 24 (n = 14) | 44 ± 7.4 (n = 27) | 14 ± 4* (n = 14) | 0.24 ± 0.04* (n = 27) | 0.08 ± 0.02 (n = 14) |
| 6 mo | 150 ± 15 (n = 27) | 233 ± 26 (n = 14) | 45 ± 7.3 (n = 27) | 20 ± 6 (n = 14) | 0.32 ± 0.07* (n = 27) | 0.06 ± 0.05 (n = 14) |
| 9-12 mo | 110 ± 19* (n = 20) | 218 ± 34 (n = 12) | 39 ± 5.8 (n = 20) | 23 ± 5 (n = 12) | 0.34 ± 0.08* (n = 20) | 0.08 ± 0.05 (n = 12) |
| 24 mo | 86 ± 14* (n = 16) | 186 ± 35 (n = 12) | 36 ± 7.2 (n = 16) | 21 ± 3.5 (n = 12) | 0.25 ± 0.07* (n = 16) | 0.10 ± 0.05 (n = 12) |

R: Responder; HR/NR: Hypo/Non-responder
*Significant p value (change from baseline)

Correlation of Cytokine Expression with Clinical Response

Linear regression analysis between cytokine levels and clinical outcome measures (ARR and EDSS) using Spearman correlation is presented in Table 6. A significant negative correlation between serum IL-10 levels on one hand and ARR and EDSS on the other hand were seen as early as 3 months and 6 months during treatment with GA. In contrast, a significant positive correlation was seen between IL-17, ARR and EDSS at 6 months of treatment. Likewise, significant negative correlations were observed in the IL-10/IL-18 and IL-10/IL-17 ratios and ARR. No significant correlation was observed between the rest of the cytokines and either ARR or EDSS (data not shown). Linear regression analysis between IL-4 as measured by ELISPOT and clinical responses using spearman correlation showed no significant correlation. However, a significant positive correlation was observed between the number of IFN-γ spots and ARR (p=0.02). A significant negative correlation between ARR and IL-4/IFN-γ ratio was also observed.

Analysis of Predictive Value of Early Biomarkers

The predictive value of the different biomarkers used in this study are shown in Table 7. The sensitivity, specificity, positive predictive value (PPV) and negative predictive value (NPV) were analyzed to determine the usefulness of the different biomarkers for potential clinical application. The sensitivity of the test is defined as the proportion of clinical responders who are correctly identified as such. The specificity on the other hand measures the proportion of negatives which are correctly identified. The PPV of a test is defined as the proportion of patients with positive test results who are correctly identified, whereas the NPV of a test is the proportion of patients with negative test results who are correctly identified. The mean cytokine levels (Mean+1 SD and or Mean+2 SD) at baseline (pre-treatment) were used as starting points to which individual cytokines were compared at each treatment time point. The IL-4/IFN-γ ratio measured by ELISPOT was significantly increased in GA-R but not in GA-HR/NR at all treatment time points producing a positive predictive value (PPV) of 80% and a specificity of 93%. Compared to pre-treatment, serum and supernatant IL-10 levels were significantly higher in GA-R at 6 months during therapy (p=0.01) with a PPV of 84%. Conversely, an IL-10 serum level below 52 pg/ml at 6 months treatment predicted non-response to GA with 94% specificity. Interleukin-17 measured in polyclonally activated PBMC showed a PPV of 75% and a specificity of 97%. Interestingly, when the IL-10/IL-18 ratios in serum and IL-10/IL-17 ratios in supernatant were measured to predict responses to the drug, it produced a sensitivity of 62%, a specificity of 93% and 95% PPV. An IL-10/IL-18 ratio in the serum below 0.74 predicted non-response to the drug with 62% sensitivity, however, an IL-10/IL-17 ratio below 2.03 predicted non-response to the drug with 96% specificity.

TABLE 6

Spearman correlations of cytokine levels with clinical outcome at 2 years of treatment with GA.

| | | CLINICAL RESPONSE AT 2 YEARS | | | |
|---|---|---|---|---|---|
| | | ARR | | EDSS | |
| CYTOKINE (Time Point) | N | $r^2$ | p-value | $r^2$ | p-value |
| IL-10 (3 mo) | 47 | 0.11 | 0.02 | 0.0008 | >0.05 |
| (6 mo) | 43 | 0.103 | 0.03 | 0.121 | 0.02 |

TABLE 6-continued

Spearman correlations of cytokine levels with clinical outcome at 2 years of treatment with GA.

| | | CLINICAL RESPONSE AT 2 YEARS | | | |
|---|---|---|---|---|---|
| | | ARR | | EDSS | |
| CYTOKINE (Time Point) | N | $r^2$ | p-value | $r^2$ | p-value |
| IL-17 (6 mo) | 20 | 0.758 | <0.01 | 0.375 | 0.004 |
| IL-10/IL-18 Ratio (6 mo) | 29 | 0.21 | 0.01 | 0.002 | 0.78 |
| IL-10/IL-17 Ratio (6 mo) | 20 | 0.2 | <0.01 | 0.002 | 0.82 |
| IFN-γ | 41 | 0.107 | 0.08 | 0.21 | 0.002 |
| IL-4 | 41 | 0.043 | >0.05 | 0.008 | 0.86 |
| IL-4/IFN-γ Ratio | 41 | 0.118 | 0.008 | 0.008 | 0.218 |

TABLE 7

Sensitivity, Specificity, PPV and NPV of different biomarkers used in the study.

| POTENTIAL BIOMARKER | TIMEPOINT DURING TREATMENT | BASELINE + 18 D | | | | BASELINE + 25 D | | | |
|---|---|---|---|---|---|---|---|---|---|
| | | SENSITIVITY | SPECIFICITY | PPV | NPV | SENSITIVITY | SPECIFICITY | PPV | NPV |
| SERUM | | | | | | | | | |
| IL 10 | 3 mo | 17% | 88% | 75% | 34% | 11% | 94% | 80% | 34% |
| | 6 mo | 30% | 93% | 91% | 38% | 21% | 93% | 88% | 35% |
| Caspase-1 | 3 mo | 6% | 96% | 50% | 84% | 6% | 96% | 50% | 64% |
| | 6 mo | 8% | 96% | 50% | 72% | 8% | 96% | 50% | 73% |
| IL-18 | 3 mo | 21% | 82% | 38% | 68% | 7% | 96% | 50% | 68% |
| | 6 mo | 17% | 86% | 33% | 71% | 8% | 96% | 50% | 72% |
| IL 10/IL 18 Ratio | 3 mo | 18% | 92% | 83% | 32% | 11% | 92% | 75% | 30% |
| | 6 mo | 62% | 93% | 95% | 54% | 41% | 93% | 95% | 43% |
| SUPERNATANT | | | | | | | | | |
| IL-10 | 3 mo | 19% | 96% | 86% | 48% | 9% | 96% | 75% | 52% |
| | 6 mo | 38% | 92% | 86% | 60% | 34% | 96% | 92% | 60% |
| IL-17 | 3 mo | 4% | 97% | 50% | 56% | 8% | 97% | 67% | 49% |
| | 6 mo | 12% | 97% | 75% | 58% | 8% | 97% | 67% | 51% |
| IL-10/IL-17 Ratio | 3 mo | 34% | 88% | 79% | 51% | 22% | 96% | 88% | 49% |
| | 6 mo | 47% | 92% | 88% | 58% | 28% | 96% | 90% | 51% |
| BONF | | 22% | 96% | 88% | 49% | 9% | 96% | 75% | 45% |
| | 6 mo | 16% | 96% | 83% | 47% | 6% | 96% | 67% | 44% |
| ELISPOT | | | | | | | | | |
| IL-4/IFN-γ Ratio | 3 mo | 52% | 71% | 78% | 43% | 15% | 93% | 80% | 36% |
| | 6 mo | 41% | 93% | 92% | 45% | 26% | 93% | 87% | 39% |

Example 2

Figure 6A:
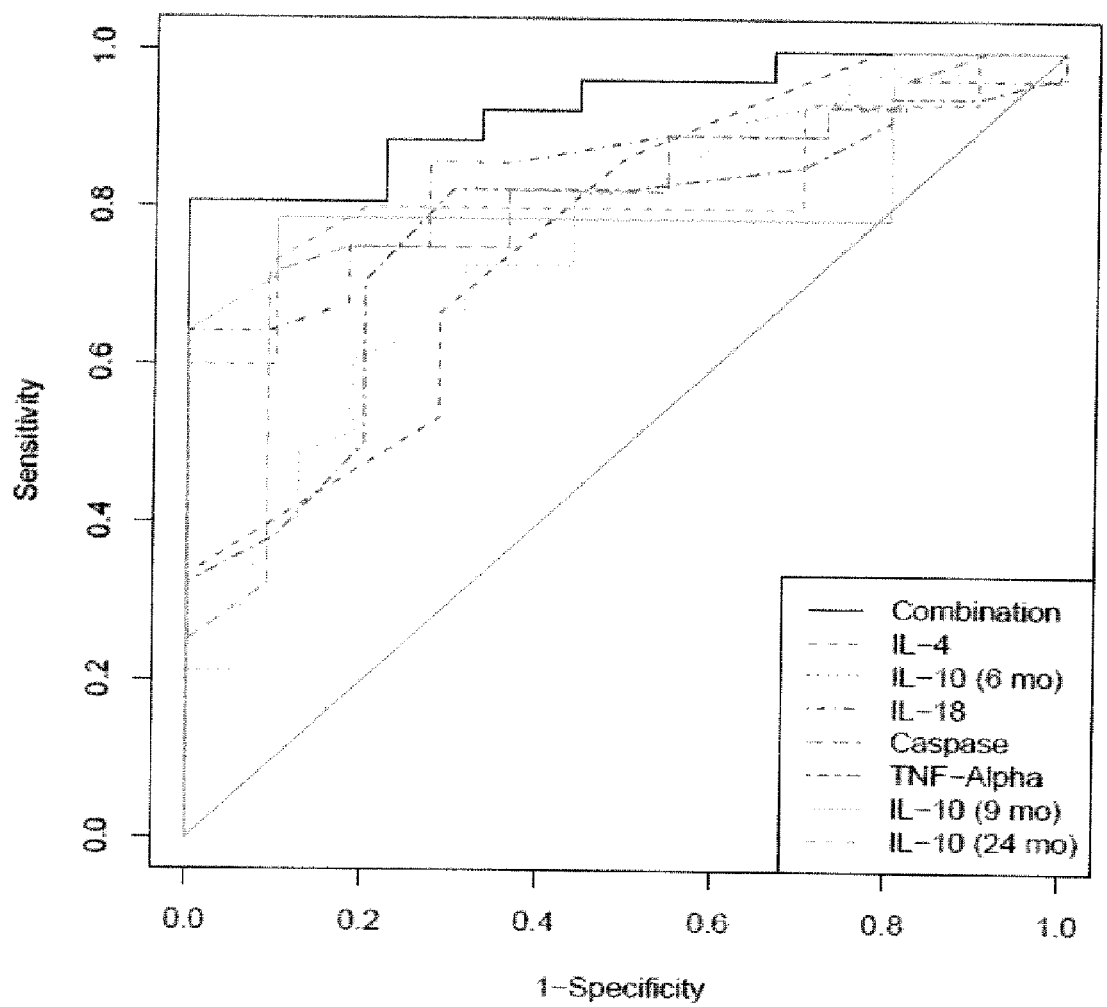
Figure 6B:
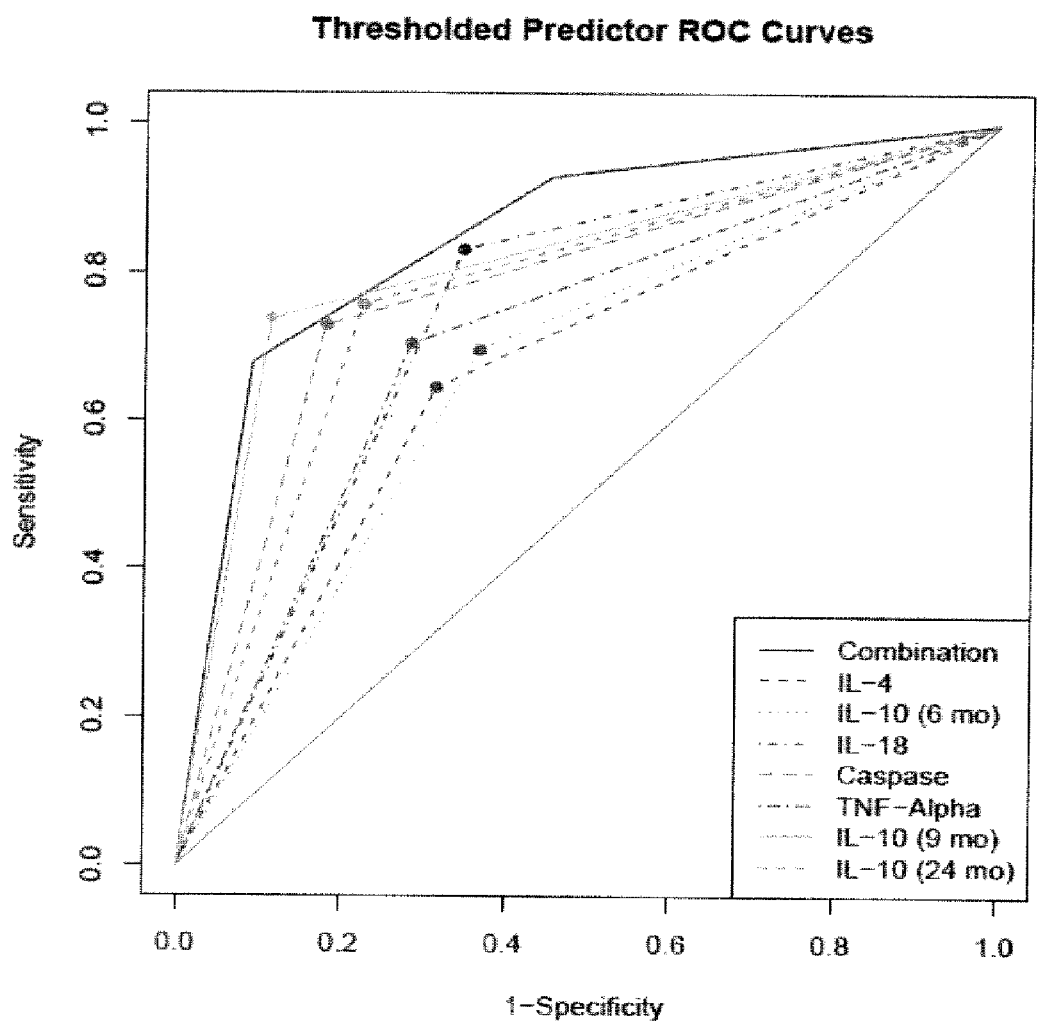

Evaluating Predictive Value of Biomarkers in Response to GA Treatment in Patients Classified as GA-R or GA-HR/NR Using a Revised Statistical Methodology
Methods Pre-treatment serum levels and the change in those levels during treatment were all considered for predicting response to treatment. Because the number of markers varied among individuals, it was not possible to make direct statistical tests of the prognostic value of various markers. Instead, we used the AUC (area under the receiver operating characteristic curve) as a summary measure of that prognostic value. AUC was used to select the top performing markers. Because we wished to construct a binary predictor rather than a probability-5 based nomogram, we dichotomized each variable by using as a threshold the value minimizing the distance between the ROC plot and the upper left corner of the unit square. As the threshold were not set a priori, we used the bootstrap statistical method to determine "optimism"-corrected values of common test performance measures. This bootstrap included the threshold-determining step.
Results Table 8 shows those markers with top optimism-corrected AUC for change from baseline. Thresholds for dichotomizing these measures are also shown, along with optimism-corrected statistics of predictive performance of the dichotomized measurements. FIG. 6A-B shows the full ROC curves for these markers, along with the curve for a combination of six-month markers. IL-10 was not used in these combinations, because only 9 subjects had the full set of marker measurements. Because IL-18 and caspase clearly dominate the other dichotomized 6-month measurements, only those markers are used in the dichotomized combination test. Table 9 shows responder status by the dichotomized outcome of those two variables.

TABLE 9

Dichotomized change at 6 months of Caspase by IL-18 by responder status.

| | | Δ Caspase at 6 months | |
|---|---|---|---|
| | | Above | Below |
| Δ IL-18 at 6 months | Above | Nonresponder: 6<br>Responder: 2 | Nonresponder: 1<br>Responder: 2 |
| | Below | Nonresponder: 3<br>Responder: 5 | Nonresponder: 1<br>Responder: 19 |

Discussion

Several studies propose a mechanism by which glatiramer acetate exerts its beneficial effect. It was thus demonstrated that glatiramer acetate binds promiscuously and with high affinity to various class II MHC molecules of mouse and human origin, and can even displace antigens from the MHC antigen-binding groove. (36) In this way, the presentation of other antigens and, consequently, the persistence of inflammatory process, is down-regulated.

Recent studies also indicate that GA induces immunomodulatory activity exerted by cells of monocytic lineage including antigen presenting cells (APC) through an increase in IL-10 and reduction in IL-12 and IL-1B. (37-40) Current data also provide evidence that regulatory T-cells (Tregs) contribute to GA's therapeutic action in EAE and possibly, MS. (15) Recent reports indicate that the deficiency in $CD4^{(+)}$ $CD25^{(+)}$ $FoxP3^{(+)}$ regulatory T-cells observed in MS and EAE is restored by GA treatment. (41, 42) These findings represent a plausible explanation for GA-mediated T-cell immune modulation and may provide a useful insight into the mechanism of action of GA in EAE and MS.

There is currently no practical in vitro assay for monitoring the immunological effects of GA. However, a triad of

TABLE 8

Summary and predictive performance statistics of top serum markers. All measurements are change from baseline. Area under the ROC curve (AUC), sensitivity, specificity, positive predictive value, and negative predictive value are all optimism-corrected using the bootstrap. Bootstrap-determined 95% confidence intervals are show in parentheses. The optimum threshold was determined by minimizing the distance between the ROC plot and the upper left corner of the unit square.

| | Measure | | | | | | |
|---|---|---|---|---|---|---|---|
| | Δ IL-4<br>6 months | Δ IL-10<br>6 months | Δ IL-18<br>6 months | Δ Caspace<br>6 months | Δ TNF-alpha<br>6 months | Δ IL-10<br>9 months | Δ IL-10<br>24 months |
| Sample Size | 44 | 49 | 39 | 39 | 44 | 24 | 25 |
| Proportion Responders | 0.68 | 0.67 | 0.72 | 0.72 | 0.77 | 0.58 | 0.60 |
| AUC (Continuous) | 0.77 | 0.76 | 0.85 | 0.80 | 0.76 | 0.82 | 0.83 |
| Median (Responders) | 1 | 15 | −102 | −142.5 | −14 | 42 | 29 |
| Median (Non-Responders) | −1.5 | −1.5 | 2 | −19 | 1 | −2 | 1 |
| Optimal Threshold | >−0.5 | >3.5 | <−1.5 | <−70.5 | <−2.5 | >19.5 | >9 |
| | Dichotomized Predictors: | | | | | | |
| Sensitivity | 0.51<br>(0.35, 0.90) | 0.67<br>(0.43, 0.86) | 0.83<br>(0.53, 0.93) | 0.72<br>(0.53, 0.90) | 0.71<br>(0.46, 0.89) | 0.67<br>(0.41, 0.93) | 0.69<br>(0.39, 0.92) |
| Specificity | 0.69<br>(0.42, 0.97) | 0.64<br>(0.48, 0.92) | 0.65<br>(0.60, 1.00) | 0.82<br>(0.64, 1.00) | 0.71<br>(0.45, 1.00) | 0.89<br>(0.70, 1.00) | 0.87<br>(0.65, 1.00) |
| Positive Predictive Value | 0.79<br>(0.63, 0.99) | 0.80<br>(0.67, 0.96) | 0.82<br>(0.79, 1.00) | 0.89<br>(0.80, 1.00) | 0.86<br>(0.78, 1.00) | 0.90<br>(0.73, 1.00) | 0.90<br>(0.68, 1.00) |
| Negative Predictive Value | 0.39<br>(0.24, 0.77) | 0.48<br>(0.27, 0.75) | 0.62<br>(0.31, 0.84) | 0.53<br>(0.31, 0.79) | 0.41<br>(0.18, 0.73) | 0.66<br>(0.38, 0.92) | 0.65<br>(0.35, 0.92) |
| AUC | 0.60<br>(0.48, 0.81) | 0.65<br>(0.54, 0.83) | 0.74<br>(0.66, 0.92) | 0.77<br>(0.63, 0.92) | 0.71<br>(0.51, 0.90) | 0.78<br>(0.65, 0.95) | 0.78<br>(0.60, 0.95) | immune responses were proposed by Hohlfeld et al. that identify GA-treated from untreated patients: (1) a significant reduction of GA-induced PBMC proliferation; (2) a positive IL-4 ELISPOT response mediated predominantly by CD4 cells after stimulation with GA; and (3) an elevated IFN-gamma response partially mediated by CD8 cells after stimulation with high GA concentrations. The GA-induced changes were consistent over time and allowed correct identification of GA-treated from untreated patients. (43) In a preliminary study, we demonstrated that lymphoproliferation to GA did not differentiate GA-responders (GA-R) from GA-hypo/non-responders (GA-HR/NR). However, reduced IFN-γ expression and stable IL-4 expression in peripheral blood mononuclear cells (PBMC) and an increased IL-4/IFN-γ ratio were associated with a favorable clinical response. (44)

Since the induction of GA-specific Th2 cells is not universal among GA treated MS patients, the immunological effects of GA treatment may correlate with the clinical response. Currently, there are no biomarkers that can reliably predict the clinical response to GA. To determine whether GA-induced immunological changes in vivo can predict the clinical response to GA therapy and to develop an early useful biomarker to treatment response with GA, we conducted a prospective 2-year study in which cytokine levels, BDNF production and lymphocyte proliferation in ex-vivo PBMC of GA-treated MS patients were correlated with the clinical response to the drug at the end of at least 2 years of therapy. The laboratory personnel were blinded as to whether the patients were clinical responders or hypo/non-responders.

In addition to exerting immunomodulatory activity on antigen presenting cells (APC), most investigators currently believe that the immunomodulatory effect of GA is linked to its ability to alter T-cell differentiation, in particular promotion of Th2 polarized CD4 cells. These GA-induced cells are believed to mediate bystander immunosuppression through the induction of IL-10 producing T-regs. (45)

We and others have demonstrated that GA treatment in MS results in the induction of GA-specific T cells with a predominant Th2 phenotype both in response to GA and cross-reactive myelin antigens. (46, 47) These findings strongly suggest that the mechanism of action of GA in MS involves the induction of cross-reactive GA-specific T-cells with a predominant Th2 cytokine profile. It has been reported that an ELISPOT assay defines an immunological response profile observed among GA-treated MS patients. This immunologic profile includes a robust in vitro activation of IFN-γ producing T cells at high concentrations of GA and activation of IL-4 producing T cells over a wider range of GA concentration. (48) Although several studies have suggested that Th2 cytokine increases are one of the major effects of GA-therapy, we have observed that a decrease in IFN-γ rather than an increase in IL-4 underlies the increased IL-4/IFN-γ ratio by ELISPOT. This ratio may serve as a useful biomarker of clinical response to GA-therapy with a PPV of 80%.

The notion that Th1 cells drive the pathogenesis of MS and EAE is still widely accepted as a major player in the disease process. However, recent data have established that IL-17-producing CD4$^+$ T-cells, driven by IL-23 and referred to as Th17 cells, play a pivotal role in the pathogenesis of MS and EAE. (49, 50) A combination of TGF-beta and IL-6 induces Th17 cell lineage commitment via expression of transcription factor ROR-γ. (49) Glatiramer acetate treatment in two different models of EAE was associated with down-regulation of IL-17. In our study, IL-17 measured in polyclonally activated T-cell supernatants showed a significant reduction in GA-R but not in the GA-HR/NR of the 6 months of treatment. Interleukin-17 levels of ≥35 pg/ml at 6 months during treatment predicted a non-response to GA with a PPV of 67% and specificity of 97%.

Increasing evidence supports a crucial role for IL-10 in the regulation of disease activity in EAE and MS by down-regulation of various pro-inflammatory cytokines such as IFN-γ, IL-18, IL-17, TNF-α, IL-6 and IL-12 among others. It has also been shown that IL-10 reduces the severity of EAE, and IL-10 deficient mice manifest more severe disease. (51-53) The beneficial effect of IL-10 in MS is believed to be due to its ability to inhibit T-cell proliferation, macrophage activation, induction of T-cell anergy and regulatory T-cell production. (54-56) Interestingly, Viera et al. recently reported that GA promotes Th2 cell development and increased IL-10 production through modulation of dendritic cells. (38) These cells have been recently characterized as IL-10 secreting Tr1-like regulatory T cells that have the ability to mediate suppression of autoimmune disease which have been found to be defective in MS. (57) The ability of IL-10 to inhibit macrophage activation is partly due to reduced expression of class II MHC molecules and reduced expression of costimulatory molecules, resulting in a reduction of T-cell mediated immune inflammation through down-regulation of pro-inflammatory cytokines.

Compared to pre-treatment, serum and supernatant IL-10 levels were significantly higher in GA-R at 6 months during therapy with a PPV of 91%. Conversely, an IL-10 serum level below 52 pg/ml at 6-month treatment predicted non-response to GA with 90% sensitivity. The predictive values of IL-10 combined with IL-18 (IL-10/IL-18 ratio) and IL-17 (IL-10/IL-17 ratio) of clinical response to GA were 95% and 90% respectively. An IL-10/IL-18 ratio in the serum below 0.74 and an IL-10/IL-17 ratio in the supernatant below 2.03 predicted non-response to GA with 93% and 92% specificity respectively.

It has been reported that GA is able to induce BDNF in PBMC that could exert effects on neuronal survival, neurotransmitter release and dendritic growth. It can also potentially rescue injured or degenerating neurons and induce axonal growth, remyelination and regeneration. (58) Detectable levels of BDNF were observed at pre-treatment with and without stimulation, consistent with previous reports. (59-61) Serum BDNF did not differentiate GA-R from GA-HR/NR, however, BDNF levels in the supernatant of GA-stimulated cells showed a significant increase among GA-R at 3 months into treatment that was not observed among the GA-HR/NR group. Interestingly, GA used as a stimulus to induce BDNF production showed a slightly higher level compared to TT, consistent with an earlier published report. (62)

No difference was seen in the lymphoproliferative response among GA-R and GA-HR-NR. This corroborates other's findings that proliferation assays are not sensitive enough measure to detect differences between responders and non-responders to the drug. (62-63)

In summary, we have shown that a reduction in IL-17, IL-18 and caspase-1, increased supernatant BDNF, increase in IL-4/IFN-γ ELISPOT ratio, and increase in serum IL-10 levels were associated with a favorable clinical response to GA therapy. The down-regulation of IL-18, IL-17 and IFN-γ can be possibly due to the induction of IL-10 that we observed during GA therapy. We have demonstrated recently a correlation between serum IL-10 levels and enhanced CD4$^+$ CD25$^+$ T-reg cell number during GA therapy. (64) We hypothesize that responders to GA produce a unique subset of IL-10-secreting T-cells with regulatory function. This could potentially explain the difference observed between GA-R and GA-HR/NR in this study.

There are 2 different classes of T-regs within the CD4+ T cell subsets: a CD4+ CD25− IL-10 producing, type-1 regulatory T cells (Tr1) and CD4+CD25+ T-reg cells. The Tr1 cells arise from naïve precursors and can be induced in vivo or in vitro from naïve T-cells by immunosuppressive drugs. The Tr1 subset is characterized by a distinct cytokine profile and is associated with increased IL-10 production upon activation. We therefore hypothesize that APCs, upon encounter with GA are activated in an antigen-specific manner. Upon activation, APCs produce a preferential skewing of naïve precursor cells into Tr1 type cell with bystander suppressive function mediated by local release of IL-10. We presume that GA-specific Tr1 cells are generated in GA-R after exposure to the drug as evidenced by a stable increase in IL-10 production. On the contrary, lack of IL-10 induction among GA-HR/NR during treatment is indicative of minimal Tr1 expression in this group.

Our data suggests that cytokine assays in sera, PBMC supernatants and cellular expression (ELISPOT) after 3-6 months of initiating GA therapy can predict responders from non-responders at least 2 years into the future (Table 7). For example, an increase in serum IL-10 level at 6 months into treatment compared to baseline has an 88% PPV and 93% specificity. Other assays such as cytokine measurement in stimulated PBMC supernatant or ELISPOTS, although more complex and less practical to perform, has potential to serve as predictive biomarkers of GA-therapy. These results provide impetus for validating the potential biomarkers described in this study against other clinical outcome measures such as magnetic resonance imaging (MRI) and the multiple sclerosis functional composite (MSFC). It is also important to determine the validity of these potential biomarkers in the long run. This would require clinical follow-ups beyond 2 years.

REFERENCES

1. Noseworthy J H, Lucchinetti C, Rodriguez M, Weinshenker B G. Multiple sclerosis. N Engl J Med 2000; 343:938-52.
2. Guideline on clinical investigation of medicinal products for the treatment of multiple sclerosis EMEA, London 16 Sep. 2006.
3. Bjartmar C, Fox R J. Pathological mechanisms and disease progression of multiple sclerosis: therapeutic implications. Drugs of Today 2002; 38:17-29.
4. Fleming J O. Diagnosis and management of multiple sclerosis. 1st ed. New York: Professional communications, Inc., 2002.
5. Anderson O W, Ellenberg J H, Leventhal C M et al. Revised estimate of the prevalence of multiple sclerosis in the United States. Ann Neurol 1992; 31:333-36.
6. Compston A, Lassmann H, McDonald I. The story of multiple sclerosis. In: Compston A, Confavreux C, Lassman H, Mcdonald I, Miller D, Noseworthy J H, Smith K, Wekerle H, editors. McAlpine's Multiple Sclerosis. London: Churchill Livingstone; 2006. p. 3-68.
7. Revel M., Pharmacol. Ther., 100(1):49-62 (2003).
8. Martinelli B F, Rovaris M, Johnson K P, Miller A, Wolinsky J S, Ladkani D, Shifroni G, Comi G, Filippi M. Effects of glatiramer acetate on relapse rate and accumulated disability in multiple sclerosis: meta-analysis of three double-blind, randomized, placebo-controlled clinical trials. Mult Scler. 2003 August; 9(4):349-55.
9. Mikol D D, Barkhof F, Chang P, Coyle P K, Jeffery D R, Schwid S R, Stubinski B, Uitdehaag B M; REGARD study group. Lancet Neurol. 2008 October; 7(10):903-14. Epub 2008 Sep. 11.
10. BECOME TRIAL, Presented at the 23rd Congress of the European Committee for Treatment and Research in Multiple Sclerosis (ECTRIMS) in Prague, Czech Republic.
11. Comi G, Filippi M and Wolinsky J S. European/Canadian multi-center, double-blind randomized, placebo controlled study of the effects of glatiramer acetate on magnetic resonance imaging-measured disease activity and burden in patients with relapsing-remitting multiple sclerosis. Ann Neurol 2001; (49):290-297.
12. Fridkis H M, Aharoni R, Teitelbaum D, Arnon R, Sela M, Strominger J L. Binding of random copolymers of three amino acids to class II MHC molecules. Int. Immunol. 1999 May; 11(5):635-41.
13. Dhib-Jalbut S S, Zhan M, Johnson K P, Martin R. Glatiramer acetate reactive blood mononuclear cells respond to myelin antigens with a Th-2 biased phenotype. J Neuroimmunology 2003; 140:163-171.
14. Chen M, Gran B, Costello K, Johnson K P, Martin R, Dhib-Jalbut S. Glatiramer acetate induces a Th-2 biased response and cross-reactivity with myelin basic protein in patients with MS. Multiple Sclerosis 2001; 7:209-219.
15. Weber M S, Prod'homme T, Youssef S, Dunn S E, Rundle C D, Lee L, Patarroyo J C, Stüve O, Sobel R A, Steinman L, Zamvil S S. Type II monocytes modulate T cell-mediated central nervous system autoimmune disease. Nat Med (2007) 13:935-943.
16. Aharoni R, Kayhan B, Eilam R, Sela M, and Arnon R. Glatiramer acetate-specific T cells in the brain express T helper 2/3 cytokines and brain-derived neurotrophic factor in situ. PNAS August 2003; 100(24):14157-62.
17. Sarchielli P, Zaffaroni M, Floridi A, Greco L, Candeliere A, Mattioni A, Tenaglia S, Di Filippo M, Calabresi P. Production of brain-derived neurotrophic factor by mononuclear cells of patients with multiple sclerosis treated with glatiramer acetate, interferon-beta 1a, and high doses of immunoglobulins. Mult Scler 2007 April; 13(3):313-31. Epub 2007 Jan. 29.
18. Bornstein, M B, Miller, A, Slagle, S, et al. A pilot trial of Cop 1 in exacerbating remitting multiple sclerosis. *New Eng J Med* 1987; 317: 408-14.
19. Comi, G, Fillippi, M, Wolinsky, J S, et al. European/Canadian multicenter, double-blind, randomized, placebo-controlled study of the effects of glatiramer acetate on magnetic resonance imagine-measured disease activity and burden in patients with relapsing multiple sclerosis. *Ann Neurol* 2001; 49: 290-7.
20. Johnson, K P, Brooks, B R, Cohen, J A, et al. Extended use of glatiramer acetate (Copaxone) is well tolerated and maintains its clinical effect on multiple sclerosis relapse rate and degree of disability. *Neurology* 1998; 50:701-8.
21. Bornstein, M B, Miller, A, Slagle, S, et al. A placebo-controlled, double-blind, randomized, two-center, pilot trial of Cop-1 in chronic progressive multiple sclerosis. *Neurology* 1991; 41: 533-39.
22. Wolinsky, J S, Narayana, P A, O'Conner, P, et al. Glatiramer acetate in primary progressive multiple sclerosis: Results of a multinational, multicenter, double-blind, placebo-controlled trial. *Ann Neurol* 2007; 61:14-24.
23. Comi G, Filippi M, Treatment with glatiramer acetate delays conversion to clinically definite multiple sclerosis (CDMS) in patients with clinically isolated syndromes (CIS). *Neurology* 2008; 71 (2): 153.

24. Tselis, A, Khan, O, Lisak, R P, Glatiramer acetate in the treatment of multiple sclerosis. *Neuropsychiatric Dis Treat* 2007; 3(2):259-67.

25. Wolinsky, J S, The use of glatiramer acetate in the treatment of multiple sclerosis. *Adv Neurol* 2006; 273-92.

26. Comi G, Cohen J A, Filippi M, Results from a phase III, one-year, randomized, double-blind, parallel-group, dose-comparison study with glatiramer acetate in relapsing-remitting multiple sclerosis. *Mult Scler* 2008; 14(suppl 1):S299.

27. Comi G, Filippi M. Presented at: 60th Annual Meeting of the American Academy of Neurology: April 12-19; Chicago, Ill. Abstract LBS.003.

28. Johnson D, Hafler D A, Fallis R J, Lees M B, Brady R O, Quarles R H, Weiner H L., "Cell-mediated immunity to myelin-associated glycoprotein, proteolipid protein, and myelin basic protein in multiple sclerosis.", *J Neuroimmunol.* 1986 November; 13 (1):99-108.

29. Brex P A et al., "A longitudinal study of abnormalities on MRI and disability from multiple sclerosis", *N Engl J Med* 2002 Jan. 17, 346(3):158-64.

30. Frohman E M et al., "The utility of MRI in suspected MS: report of the Therapeutics and Technology Assessment Subcommittee of the American Academy of Neurology", *Neurology,* 2003, Sep. 9, 61(5):602-11.

31. Fridkis-Hareli M, Santambrogio L, Stern J N, Fugger L, Brosnan C, Strominger J L. Novel synthetic amino acid copolymers that inhibit autoantigen-specific T cell responses and suppress experimental autoimmune encephalomyelitis. J Clin Invest 109: 1635-1643 (2002).

32. Fridkis-Hareli M, Neveu J M, Robinson R A, Lane W S, Gauthier L, Wucherpfennig K W, Sela M, Strominger J L. Binding motifs of copolymer 1 to multiple sclerosis- and rheumatoid arthritis-associated HLA-DR molecules. J Immunol 162: 4697-4704 (1999).

33. W I McDonald, A Compston, G Edan, D Goodkin, H P Hartung, F D Lublin H F Mcfarland, D W Paty, C H Polman, S C Reingold, M Sanderberg-Wollheim, W Sibley, A Thompson, S Vandernoort, B Y Weinshenker, J S Wolinsky, Recommended diagnostic Criteria for multiple sclerosis: Guidelines from the international panel on the diagnosis of multiple sclerosis, Neurology 5 (2001), pp 121-127.

34. Cohen B A, Khan O, Jeffery D R, Bashir K, Rizvi S A, Fox E J, Agius M, Bashir R, Collins T E, Herndon R, Kinkel P, Mikol D D, Picone M A, Rivera V, Tornatore C, Zwibel H. Identifying and treating patients with suboptimal responses. Neurology 2004 Dec. 28; 63(12 Suppl 6):S33-40.

35. Felderhoff-Mueser U. Schmidt O I, Oberholzer A, Buhrer C, and Stahel P F. IL-18: a key player in neuroinflammation and neurodegeneration. Trends in Neuroscience. Vol 28, Issue 9, September 2005, 487-493.

36. Fridkis-Hareli M, Teitelbaum D, Gurevich E, et al. Direct binding of myelin basic protein and synthetic copolymer 1 to class II major histocompatibility complex molecules on living antigen-presenting cells-specificity and promiscuity. Proc. Natl. Acad. Sci. USA. 91: 4872-6 (1994).

37. Kim H J, Ifergan I, Antel J P, Sequin R, Duddy M, Lapierre Y, Jalili F, Bar-Or A. Type 2 monocytes and microglia differentiation mediated by glatiramer acetate therapy in patients with multiple sclerosis. J Immunol (2004) 172:7144-7153.

38. Vieira P L, Heystek H C, Wormmeester J, Wierenga E A, Kapsenberg M L. Glatiramer acetate (copolymer-1, copaxone) promotes Th2 cell development and increased IL-10 production through modulation of dendritic cells. J Immunol (2003) 170:4483-4488.

39. Hussein Y, Sanna A, Soderstrom M, Link H, Huanq Y M. Glatiramer acetate and IFN-beta act on dendritic cells in multiple sclerosis. J Neuro Immunol (2001)121:102-110.

40. Daniella B, Nicolas M, Martin S W, Karim J B, Mahdia B, Lyssia G, Michel C, Scott Z, Patrice H L. Glatiramer acetate increases IL-B receptor antagonist but decreases T cell-induced IL-B in human monocytes and multiple sclerosis. PNAS (2009) Early Edition 0812183106.

41. Jee Y, Piao W H, Liu R, Bai X F, Rhodes S, Rodebaugh R, Campagnolo D I, Shi F D, Vollmer T L. CD4(+)CD25(+) regulatory T cells contribute to the therapeutic effects of glatiramer acetate in experimental autoimmune encephalomyelitis. Clin Immunol 2007 October; 125(1): 34-42. Epub 2007 Jul. 16.

42. Hong J, Li N, Zhang X, Zheng B, Zhang J Z. Induction of CD4+CD25+ regulatory T cells by copolymer-I through activation of transcription factor Foxp3. Proc Natl Acad Sci 2005 May 3; 102(18):6449-54. Epub 2005 Apr. 25.

43. Farina C, Then Bergh F, Albrecht H, Meinl E, Yassouridis A, Neuhaus O, Hohlfeld R. Treatment of multiple sclerosis with Copaxone (COP): Elispot assay detects COP-induced interleukin-4 and interferon-gamma response in blood cells. Brain. 2001 April; 124(Pt 4):705-19.

44. Valenzuela R M, Costello K, Chen M, Said A, Johson K P, Dhib-Jalbut S. Clinical response to glatiramer acetate correlates with modulation of IFN-gamma and IL-4 expression in multiple sclerosis. Mult Scler. 2007 July; 13(6):754-62.

45. Stern J N H, Keskin D, Zanh H, Huijuan L, Zenichiro K, and Strominger J. Amino acid copolymer-specific IL-10 secreting regulatory T-cells that ameliorate autoimmune disease in mice. PNAS 2008, 15(13):5172-5176.

46. Dhib-Jalbut S S, Zhan M, Johnson K P, Martin R. Glatiramer acetate reactive blood mononuclear cells respond to myelin antigens with a Th-2 biased phenotype. J Neuroimmunology 2003; 140:163-171.

47. Chen M, Gran B, Costello K, Johnson K P, Martin R, Dhib-Jalbut S S. Glatiramer acetate induces a Th-2 biased response and crossreactivity with myelin basic protein in patients with MS. Multiple Sclerosis 2001; 7:209-219.

48. Farina C, Wagenpfeil S, Hohlfeld R. Immunological assay for assessing the efficacy of glatiramer acetate (Copaxone) in multiple sclerosis. A pilot study. J Neurol. 2002 November; 249(11):1587-92.

49. Aranami T, Yamamura T. Th17 Cells and autoimmune encephalomyelitis (EAE/MS). Allergol Int. 2008 June; 57(2):115-20.

50. Begum-Haque S, Sharma A, Kasper I R, Foureau D M, Mielcarz D W, Haque A, Kasper L H. Downregulation of IL-17 and IL-6 in the central nervous system by glatiramer acetate in experimental autoimmune encephalomyelitis. J Neuroimmunol. 2008 Nov. 15; 204(1-2):58-65.

51. Rott O, Fliescher B, Cash E. Interleukin 10 prevents experimental allergic encephalomyelitis in rats. Eur. J. Immunol 24(1994):1434-1440.

52. Cua D J, Groux H, Hinton D R, Stohlman S A, Coffman R L. Transgenic Interleukin-10 prevents induction of experimental autoimmune encephalomyelitis. J. Exp. Med. 189 (1999):1005-1010.

53. Beebe A M, Cua D J, Waal Malefyt R. de. The role of IL-10 in autoimmune disease: systemic lupus erythematosus (SLE) and multiple sclerosis (MS), Cytokine Growth factor rev. 12 (2002):403-412.

54. Imitola J, Chitnis and Khoury S J. Cytokines in multiple sclerosis: from bench to bedside, Pharmacol. Ther. 106 (2005):163-177.
55. Groux H, Bigler M, De Vries J E and Roncarolo M G. Interleukin-10 induces a long-term antigen specific anergic state in human CD4+ T cells. J. exp. Med. 184 (1996):19-29
56. Roncarlo M G, Bachetta R, Bordignon C, Narula S, Levings M K. Type-1 regulatory cells. Immunol. Rev. 182(2002):68-80.
57. Martinez Forero I, Garcia-Munoz R, Martinez-Pasamar S, Inoges S, Lopez-Diaz de Cerio A, Palacios R, Sepulcre J, Moreno B, Gonzalez Z, Fernadez-Diez B, Melero I, Bendandi M, Villoslada P. IL-10 suppressor activity and ex-vivo Tr1 cell function are impaired in multiple sclerosis. Eur J Immunol. 2008 February; 38(2):576-86.
58. Gravel C, Gotz R, Lorrain A and Sendtner M. Adenoviral gene transfer of ciliary neurotrophic factor and brain-derived neurotrophic factor leads to long-term survival of axotomized motor neurons Nat Med 1997; July 3(7): 765-770.
59. Caggiula M, Batocchi A P, Frisullo G, Angelucci F, Patanella A K, Sancricca et al, Neurotrophic factors and clinical recovery in RR-MS, Scand J Immunol 2005, 62: 176-82.
60. Gielen A, Khademi M, Muhallab S, olason T, Piehl F, Increased brain-derived neurotrophic factor in white blood cells or RR MS patients Scand J Immunol 2003, 57:493-97.
61. Sarchielli P, Greco L, Stipa A, Floridi A, Gallai V, Brain-derived neurotrophic factor in patients with multiple sclerosis. J Neuroimmunol 2002 November 132(1-2):180-88.
62. Sarchielli P, Zaffaroni M, Floridi A, Greco L, Candeliere A, Mattioni A, Tenaglia S, Di Filippo M, and Calabresi P. Production of brain-derived neurotrophic factor by mononuclear cells of patients with multiple sclerosis treated with glatiramer acetate, interferon-beta 1a, and high doses of immunoglobulins Multiple Sclerosis 2007; 13:313-331.
63. Valenzuela R M, Costello K, Chen M, Said A, Johnson K P, Dhib-Jalbut S. Clinical response to glatiramer acetate correlates with modulation of IFN-gamma and IL-4 expression in multiple Sclerosis. Mult Scler. 2007 April; 13(3):313-31. Epub 2007 Jan. 29.
64. Valenzuela, R M and Suhayl Dhib-Jalbut. Time course and functional capacity of glatiramer acetate (GA)-induced regulatory T-cells in multiple sclerosis patients. Poster presented at: European Committee for Treatment and Research in Multiple Sclerosis (ECTRIMS July 2007); Prague, Czech Republic.

The invention claimed is:

1. A method for treating a subject afflicted with multiple sclerosis with a pharmaceutical composition comprising glatiramer acetate and a pharmaceutically acceptable carrier, comprising the steps of:
   a) administering a therapeutic amount of the pharmaceutical composition to the subject;
   b) determining whether the subject is a glatiramer acetate responder by measuring the value of IL-10/IL-18 ratio in the blood of the subject, and comparing the measured value to a reference value to identify the subject as a glatiramer acetate responder; and
   c) continuing the administration if the subject is identified as a glatiramer acetate responder, or modifying treatment of the subject if the subject is not identified as a glatiramer acetate responder.

2. The method of claim 1, wherein an increase of IL-10/IL-18 ratio relative to the reference value is associated with a subject being a responder to glatiramer acetate treatment.

3. The method of claim 2, wherein the IL-10/IL-18 ratio is measured in the serum of the subject.

4. The method of claim 2, wherein the IL-10/IL-18 ratio is measured in the PBMC supernatant of the subject.

5. The method of claim 2, wherein the increase of IL-10/IL-18 ratio relative to the reference value is observed at 3 months after the beginning of administration of the pharmaceutical composition.

6. The method of claim 2, wherein the increase of IL-10/IL-18 ratio relative to the reference value is observed at 6 months after the beginning of administration of the pharmaceutical composition.

7. The method of claim 1, wherein at 6 months after the beginning of administration of the pharmaceutical composition the IL-10/IL-18 ratio greater than or equal to a reference value 0.74 is associated with a subject being a responder to glatiramer acetate treatment.

8. The method of claim 1, wherein at 6 months after the beginning of administration of the pharmaceutical composition the IL-10/IL-18 ratio below 0.74 is associated with a subject being a non-responder to glatiramer acetate treatment.

9. The method of claim 1, wherein step b) further comprises measuring the value of one or more biomarkers selected from the group consisting of IL-17 concentration, IL-concentration, TNF-α concentration, BDNF concentration, caspase-1 concentration, unstimulated IL-4/IFN-γ ratio and IL-10/IL-17 ratio in the blood of the subject, and comparing the measured value to a reference value of each biomarker to identify the subject as a glatiramer acetate responder.

10. The method of claim 9, wherein an increase of BDNF concentration relative to a reference value or increase of IL-10/IL-17 ratio relative to a reference value is associated with a subject being a responder to glatiramer acetate treatment.

11. The method of claim 10, wherein the increase of BDNF concentration or IL-10/IL-17 ratio is observed at 3 months after the beginning of administration of the pharmaceutical composition.

12. The method of claim 10, wherein the increase of BDNF concentration or IL-10/IL-17 ratio is observed at 6 months after the beginning of administration of the pharmaceutical composition.

13. The method of claim 9, wherein a decrease of IL-17 concentration relative to a reference value, a decrease of IL-18 concentration relative to a reference value or a decrease of caspase-1 concentration relative to a reference value is associated with a subject being a responder to glatiramer acetate treatment.

14. The method of claim 13, wherein the decrease of IL-17 concentration, IL-18 concentration of caspase-1 concentration is observed at 3 months after the beginning of administration of the pharmaceutical composition.

15. The method of claim 13, wherein the decrease of IL-17 concentration, IL-18 concentration of caspase-1 concentration is observed at 6 months after the beginning of administration of the pharmaceutical composition.

16. The method of claim 1, wherein the multiple sclerosis is relapsing remitting multiple sclerosis in subjects who have experienced a first clinical episode and have MRI features consistent with multiple sclerosis.

17. The method of claim 1, wherein the IL-10/IL-18 ratio is observed at 3 months after the beginning of administration of the pharmaceutical composition.

18. The method of claim 1, wherein the IL-10/IL-18 ratio is observed at 6 months after the beginning of administration of the pharmaceutical composition.

19. A method for treating a subject afflicted with relapsing-remitting multiple sclerosis in subjects who have experienced a first clinical episode and have MRI features consistent with multiple sclerosis with a pharmaceutical composition comprising glatiramer acetate and a pharmaceutically acceptable carrier, comprising the steps of:
 a) administering a therapeutic amount of the pharmaceutical composition to the subject;
 b) determining whether the subject is a glatiramer acetate responder by
  i) measuring the value of IL-10/IL-18 ratio in the blood of the subject, and comparing the measured value to a reference value to identify the subject as a glatiramer acetate responder, wherein an increase of IL-10/IL-18 ratio relative to the reference value is associated with a subject being a responder to glatiramer acetate treatment, wherein the value of IL-10/IL-18 ratio is measured about 3 months to about 24 months after the beginning of administration of the pharmaceutical composition, and
  ii) further measuring the value of one or more biomarkers selected from the group consisting of IL-17 concentration, IL-18 concentration, TNF-α concentration, BDNF concentration, caspase-1 concentration, unstimulated IL-4/IFN-γ ratio and IL-10/IL-17 ratio in the blood of the subject, and comparing the measured value to a reference value of each biomarker to identify the subject as a glatiramer acetate responder, wherein an increase of BDNF concentration relative to a reference value or increase of IL-10/IL-17 ratio relative to a reference value is associated with a subject being a responder to glatiramer acetate treatment, and wherein a decrease of IL-17 concentration relative to a reference value, a decrease of IL-18 concentration relative to a reference value or a decrease of caspase-1 concentration relative to a reference value is associated with a subject being a responder to glatiramer acetate treatment; and
 c) continuing the administration if the subject is identified as a glatiramer acetate responder, or modifying treatment of the subject if the subject is not identified as a glatiramer acetate responder, so as thereby to treat the subject.

* * * * *